(12) United States Patent
Nag

(10) Patent No.: US 11,107,578 B2
(45) Date of Patent: Aug. 31, 2021

(54) SYSTEMS AND METHODS FOR FACILITATING HEALTH RESEARCH

(71) Applicant: Apple Inc., Cupertino, CA (US)

(72) Inventor: Divya Nag, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 605 days.

(21) Appl. No.: 15/019,730

(22) Filed: Feb. 9, 2016

(65) Prior Publication Data

US 2016/0267238 A1    Sep. 15, 2016

Related U.S. Application Data

(60) Provisional application No. 62/129,691, filed on Mar. 6, 2015.

(51) Int. Cl.
| | | |
|---|---|---|
| *G16H 40/63* | (2018.01) | |
| *G16H 10/60* | (2018.01) | |
| *G16H 40/67* | (2018.01) | |
| *G16H 70/20* | (2018.01) | |

(52) U.S. Cl.
CPC ............. *G16H 40/63* (2018.01); *G16H 10/60* (2018.01); *G16H 40/67* (2018.01); *G16H 70/20* (2018.01)

(58) Field of Classification Search
CPC .. G16H 10/00–65; G16H 40/63; G16H 40/67; G16H 70/20; G06F 19/3418; G06Q 50/22–24
USPC .......................................................... 705/2–3
See application file for complete search history.

(56) References Cited

U.S. PATENT DOCUMENTS

| | | | |
|---|---|---|---|
| 6,820,057 B1 | 11/2004 | Loch et al. | |
| 8,005,691 B2 | 8/2011 | Kumar et al. | |
| 8,157,730 B2 * | 4/2012 | LeBoeuf ................ | G16H 10/60 600/300 |
| 8,423,387 B1 | 4/2013 | Mirza | |
| 8,712,510 B2 * | 4/2014 | Quy ...................... | A61B 5/6838 600/520 |
| 8,715,181 B2 | 5/2014 | Brynelsen et al. | |
| 8,737,971 B2 | 5/2014 | Van Rooyen et al. | |
| (Continued) | | | |

FOREIGN PATENT DOCUMENTS

| | | |
|---|---|---|
| CN | 101393520 A | 3/2009 |
| CN | 101667224 A | 3/2010 |
| (Continued) | | |

OTHER PUBLICATIONS

"Non-Final Office Action", U.S. Appl. No. 15/014,856, dated Nov. 15, 2018, 17 pages.

(Continued)

*Primary Examiner* — Michael Tomaszewski

(74) *Attorney, Agent, or Firm* — Kilpatrick Townsend & Stockton LLP

(57) ABSTRACT

Methods and systems for facilitating health research through enhanced communication between research participants and researchers. Methods include communication of information related to a research study to a portable computing device of a research participant by use of an application framework and one or more modules. The one or more modules may be provided with the application framework or may include one or more modules from third-party researchers so as to allow standardization of communication from multiple research studies and differing research facilities.

36 Claims, 26 Drawing Sheets

(56) References Cited

U.S. PATENT DOCUMENTS

| | | | |
|---|---|---|---|
| 8,818,823 B2 | 8/2014 | Ackerson et al. | |
| 8,930,221 B2 | 1/2015 | Patterson et al. | |
| 8,961,414 B2 * | 2/2015 | Teller | G16H 20/30 600/301 |
| 9,014,779 B2 | 4/2015 | Hutchison et al. | |
| 9,582,642 B2 * | 2/2017 | Keen | G06F 16/22 |
| 2001/0032100 A1 | 10/2001 | Mahmud et al. | |
| 2002/0005935 A1 | 1/2002 | Robin | |
| 2003/0028400 A1 | 2/2003 | Christ et al. | |
| 2003/0074221 A1 | 4/2003 | Christ et al. | |
| 2003/0195774 A1 * | 10/2003 | Abbo | G16H 10/60 705/3 |
| 2004/0054760 A1 | 3/2004 | Ewing et al. | |
| 2005/0049898 A1 | 3/2005 | Hirakawa | |
| 2005/0197903 A1 * | 9/2005 | Hoffman | G06F 19/3456 705/2 |
| 2006/0064030 A1 | 3/2006 | Cosentino et al. | |
| 2006/0248593 A1 | 11/2006 | Dennis et al. | |
| 2006/0282292 A1 * | 12/2006 | Brink | G16H 10/60 705/3 |
| 2010/0120585 A1 * | 5/2010 | Quy | G16H 40/67 482/8 |
| 2011/0295616 A1 | 12/2011 | Vesto | |
| 2012/0101847 A1 | 4/2012 | Johnson et al. | |
| 2012/0313776 A1 | 12/2012 | Utter et al. | |
| 2013/0030836 A1 * | 1/2013 | Ackerson | G06Q 50/24 705/3 |
| 2013/0064358 A1 | 3/2013 | Nusbaum | |
| 2013/0197942 A1 | 8/2013 | Chiu et al. | |
| 2013/0275151 A1 | 10/2013 | Moore et al. | |
| 2013/0304511 A1 | 11/2013 | Gunter | |
| 2014/0081662 A1 | 3/2014 | Bradrick et al. | |
| 2014/0122125 A1 | 5/2014 | Deshpande et al. | |
| 2014/0135592 A1 | 5/2014 | Ohnemus et al. | |
| 2014/0242698 A1 | 8/2014 | Smith | |
| 2014/0257851 A1 | 9/2014 | Walker et al. | |
| 2014/0276552 A1 | 9/2014 | Nguyen et al. | |
| 2014/0278474 A1 | 9/2014 | McClure et al. | |
| 2015/0242592 A1 | 8/2015 | Weiss et al. | |
| 2015/0244852 A1 | 8/2015 | Erickson et al. | |
| 2015/0294090 A1 * | 10/2015 | Kodiyan | G06F 19/00 705/2 |
| 2015/0347499 A1 | 12/2015 | Keen et al. | |
| 2015/0347684 A1 | 12/2015 | Keen et al. | |
| 2015/0347690 A1 | 12/2015 | Keen et al. | |
| 2015/0347784 A1 | 12/2015 | Keen | |
| 2016/0210416 A1 | 7/2016 | Whitehurst | |
| 2016/0301792 A1 | 10/2016 | Lee et al. | |
| 2017/0011182 A1 | 1/2017 | Whitehurst | |

FOREIGN PATENT DOCUMENTS

| | | |
|---|---|---|
| CN | 103182175 A | 7/2013 |
| WO | 2015/183495 | 12/2015 |

OTHER PUBLICATIONS

"Office Action", China Patent Application No. 201580028726.9, dated Jul. 31, 2017, 15 pages.

* cited by examiner

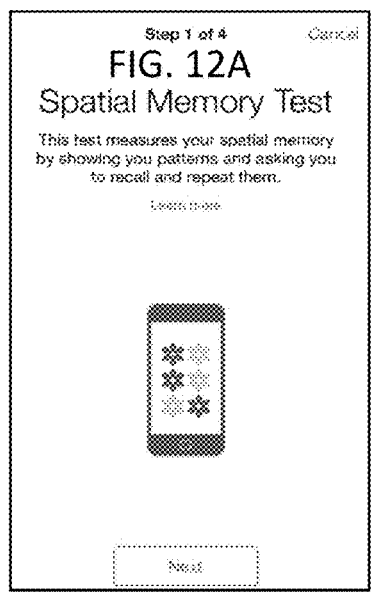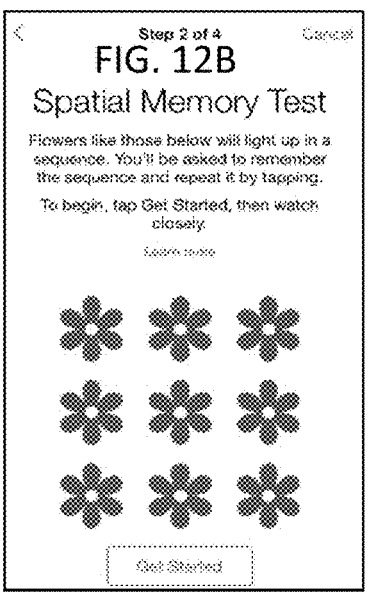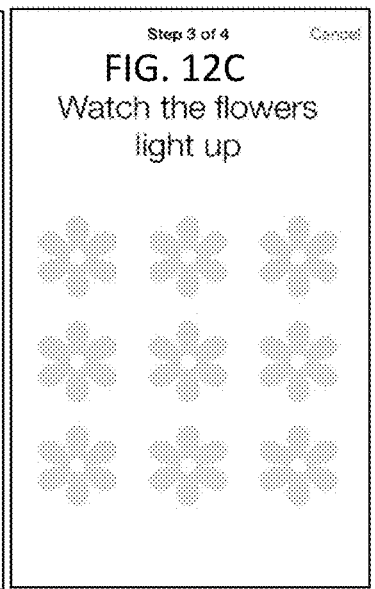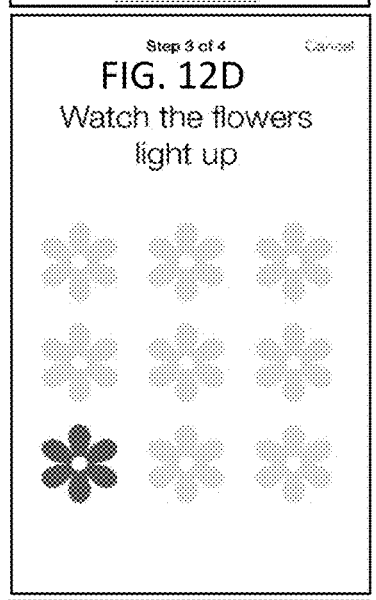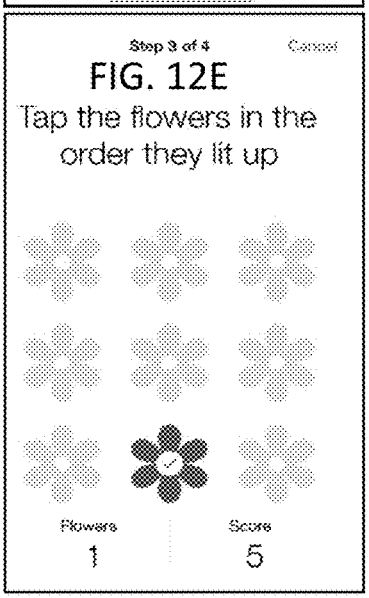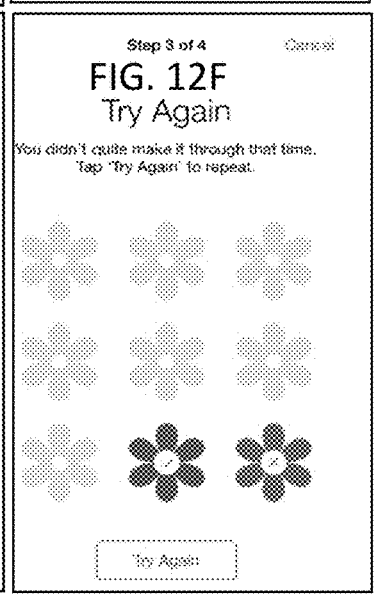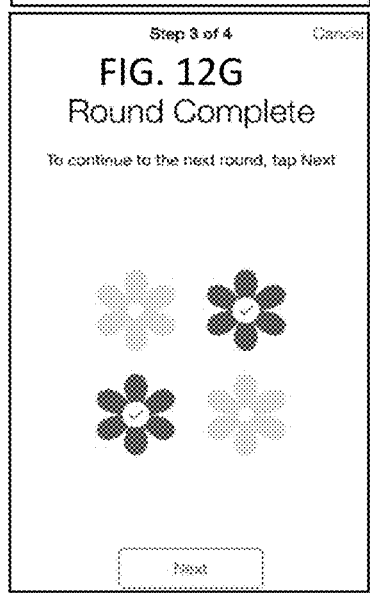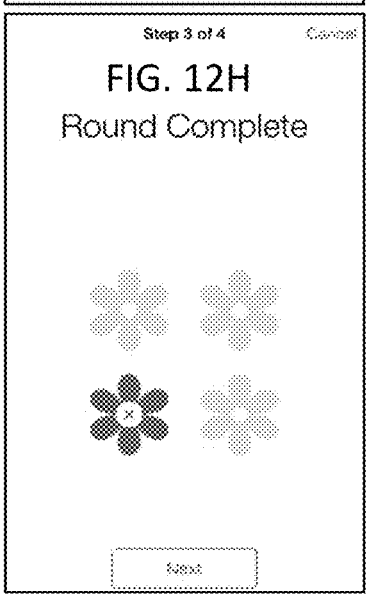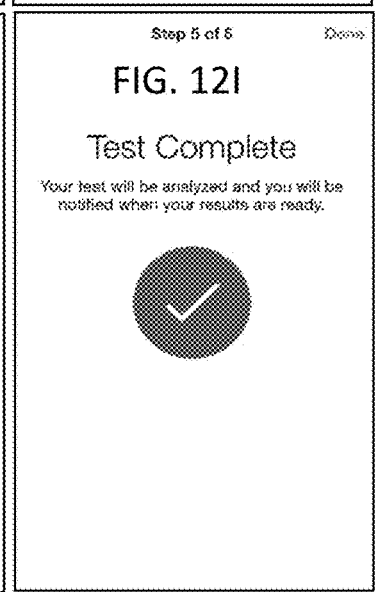

SYSTEMS AND METHODS FOR FACILITATING HEALTH RESEARCH

CROSS REFERENCES TO RELATED APPLICATIONS

The present application claims the benefit under 35 USC §119(e) of U.S. Provisional Appln. No. 62/129,691 filed Mar. 6, 2015; the full disclosure which is incorporated herein by reference in its entirety for all purposes.

The present application is related to U.S. 62/006,031 filed May 30, 2014; U.S. Ser. No. 14/499,449 filed Sep. 29, 2014; and U.S. Ser. No. 14/499,519 filed Sep. 29, 2014; the entire contents of each are hereby incorporated by reference for all purposes.

FIELD OF INVENTION

The present invention relates to systems and methods for facilitating health research through enhanced collection and communication of health information between research participants and researchers.

BACKGROUND OF THE INVENTION

Traditionally, health research studies involve exchanges of a multitude of information between participants and researchers, usually in written form. Such studies often require an initial in-person visit to ensure informed consent is received before the study commences after which periodic or follow-up visits may be required. Current research studies can be complex and fragmented resulting in redundancies and inefficiencies in collecting data that frustrate both user and researchers. In addition, the processes by which participants are recruited, consent is obtained and research conducted varies widely between research facilities, thereby further complicating attempts to make the processes by which research is conducted more efficient.

Although the development of electronic medical record and secure communication of medical information has somewhat improved exchange of health information for purposes of treatments and research, the initial participant recruiting and consent is still typically performed in an office setting and involves review and collection of research disclosures in written form. The inconvenience of this aspect reduces the participant pool such that health research studies generally have limited, if not insufficient, numbers of participants. In recent years, acquisition of health information and various health metrics outside of the electronic medical records has increased dramatically. The usefulness of such health information, however, is limited given the complexities and burden associated with dissemination of such large amounts of information. While recruitment of health study participants and health information obtained during research studies can be improved by utilizing a wider range of health information now available, providing these improvement is challenging and often problematic given the limited time and resources available in modern healthcare in addition to heightened concerns as to user privacy.

BRIEF SUMMARY OF THE INVENTION

Methods of the present invention pertain to facilitating research by improved communication between the researchers and research participants. In one aspect, the system includes an application framework on a portable computing device of a research participant that performs various research objectives using one or more modules received within the framework.

In one aspect, the invention provides a method for facilitating health research that includes steps of: receiving, with a portable computing device, one or more modules relating to a health research study, the portable computing device associated with a user participating in the health research study; displaying, on a graphical user interface of the portable computing device, a user instruction based on a respective module of the one or more modules; receiving an input with the portable computing device in response to the instruction; and outputting to a third party health researcher the input associated with the instruction of the one or more modules for use in health research relating to the study. In some embodiments, the methods further includes a step of de-identifying the user input from the user before outputting to the third party health researcher. The portable computing device may be a smartphone, tablet, laptop, a computer and the like. Health research facilitated by such methods include observational pre-clinical, clinical, or post-clinical studies for tele-monitoring research.

In some embodiments, the input comprises a user input entered by the user on the graphical user interface of the device or an output of one or more sensors associated with the portable computing device. The one or more sensors may be incorporated into the portable computing device or may be separate from and communicatively coupled with the portable computing device. In some embodiments, the one or more sensors separate from the portable computing device include a wearable sensor device configured to detect a sensor parameter over a duration of time and transmit the detected sensor parameter to the portable computing device. Such sensors may be configured for detecting any of: activity level, activity tracking, respiration, body temperature, heart wellness data, hydration levels, perspiration, blood glucose, salinity, sleep cycles, posture, $O_2$ levels, muscle engagement, or any combination thereof. Examples of such sensors includes accelerometers, gyroscopes, microphone/audio sensors, a camera/CCD, a photoplethysmogram (PPG) sensor or any combination thereof.

In some embodiments, receiving the input comprises receiving sensor data from one or more sensors over a duration of time. In one aspect, receiving the sensor data may further include measuring a sensor parameter based on a user interaction, while in another aspect, receiving the sensor data comprises passively collected sensor data from the one or more sensors without requiring user interaction.

In one aspect, the methods utilize a portable computing device having a first-party application framework thereon, through which the one or more modules are communicated to the user. The modules may include a first set of modules that are first-party modules, developed by the same entity as the application framework, or third-party modules developed by another entity, such a third-party researcher. The modules may be configured in various different types, includes a survey module, an activity or task module, an informed consent module, or a passive data collection module. The survey modules may include a question or series of questions relating to an attribute or status of the user, a symptom experienced by the user, a temporal aspect of an activity associated with the user, or a history of medication or disease of the user. The activity or task modules may include an instruction to perform an activity concurrent with monitoring of sensor data. Examples of activity modules include a fitness test module, a gait test module, a phonation test module, a memory test module, and a finger tapping test module. The informed consent module includes a display of a description of the research study being facilitated on the portable computing device. In some embodiments, the method includes receiving a set of modules from a third-party health researcher through a server communicatively coupled with the portable device. The set of modules may include various research survey activities or data collection tasks or may include follow up questions/queries based on user input received in response to a previously performed module.

In some embodiments, the modules received by the system include a recruitment step module having one or more question steps relating to eligibility for participation in the health research study, wherein displaying the user instruction comprises requesting information of the user corresponding to eligibility as a participant. The one or more question steps may include inquiries in regard to any of: weight, age race, demographic, activity level, diet, sleep, family history, symptoms, disease status/history, medical status/characteristic/history, medication history, or any combination thereof.

In other embodiments, the modules may include a consent module that displays a user instruction that requests consent of the user, with the portable computing device, for participation in the health research study after performing the recruitment module. The consent module may include information corresponding to a consent document associated with the research study and may include a visual consent step and a consent review step. The visual consent step comprises a sequence of displays or illustrations of information relating to any of: an information survey of the research study, data gathering, privacy, use of participant data, time commitment by participant, a description of study tasks, withdrawal from the study, or any combination thereof. In some embodiments, the consent module may further include performing of an engagement test during the visual consent step, wherein the engagement test comprises: providing an instruction to move the portable computing device according to a particular movement (e.g. shaking or tilting the device) and concurrently monitoring a sensor parameter to verify performance of the instruction. In another aspect, the engagement test may involve tracking of the user's eyes to confirm eye activity consistent with actual reading of the consent disclosures. In other embodiments, the consent module may further include performing a comprehension test during the visual consent step before proceeding with the consent review step, wherein the comprehension test comprises: displaying one or more questions regarding the information displayed during the consent step and concurrently monitoring a sensor parameter that includes pressure by manual touching of the display for to verify a selected answer of the comprehension test. The consent review step may include displaying information regarding consent for the research study in accordance with applicable guidelines and displaying a consent form such that the input received with the portable computing device is indicative of consent of the user to participate in the study, for example the form may be a signature field that received an electronic signature of the user that indicates consent.

In some embodiments, the modules may include a survey test module that includes one or more question steps presented concurrent with sensing a parameter of one or more sensors. The one or more questions may correspond to a selection of any of: scale, Boolean, picked value, text choice, numerical choice, temporal value, open-ended text answer format, or any combination thereof. For example, the sensed parameter may be pressure and/or sliding movement corresponding to manual touching of a graphical display screen and the one or more sensors comprise pressure sensors within the portable computing device.

In some embodiments, the one or more modules include activity or task modules that provide instruction to perform a specific task or activity concurrent with monitoring sensor data to measure a parameter during performance of the task or activity. Such activity or task modules may include various types of tasks or activities. In one example, the activity module comprises a memory test module that includes an instruction to indicate a sequential order of an animation on a graphical user interface displace of the portable computing device concurrent with monitoring a sensed parameter from one or more sensors. For example, a plurality of items may appear or be emphasized in a particular order after which the user is instructed to mimic the order in which the items appeared by selecting the items on a graphical user display of the portable computing device. Here, the sensed parameter may be pressure and/or sliding movement corresponding to manual touching of a graphical display screen and the one or more sensors comprise pressure sensors within the portable computing device. In another example, the activity module may be a fitness test module that includes an activity task including an instruction to walk a pre-determined duration concurrent with monitoring of sensed data from one or more sensors. For example, in one embodiment, the monitored sensed data comprises heart rate measured by a PPG sensor and a rate of walking measured by an accelerometer. In yet another example, the activity module may include a speech or phonation test module including an instruction to vocalize into an audio sensor associated with the portable device concurrent with monitoring of sensed data from the audio sensor. Here, the sensed data is any of volume, duration and speech pattern or any combination thereof, the audio sensor, such as a microphone of the portable computing device. In still another example, the activity module may be a balance or gait test module including an instruction to walk and/or stand still concurrent with monitoring of sensed parameters with one or more sensors on the user. The sensed parameters may be movement and/or balance and the one or more sensors include one or more accelerometers. In still another example, the activity module may be a tapping test module for determining manual dexterity and/or coordination. Here, the sensed parameter may be pressure from manual touching of a graphical display screen of the portable computing device and the one or more sensor comprise pressure transducers of the portable computing device.

In another aspect, systems for facilitating health research are provided herein. Such system may include: a portable computing device operable by a user or an associated caretaker, the portable computing device including a wireless communication module for transmitting to and receiving data from a third-party researcher; a processor of the portable computing device, the processor having a computer readable medium having stored thereon computer executable instructions configured for: receiving one or more modules relating to a health research study; displaying, on a graphical user interface of the portable computing device, a user instruction based on a respective module of the one or more modules; receiving an input with the portable computing device in response to the instruction; and outputting to a third party health researcher the input associated with the instruction of the one or more modules for use in health research relating to the study. In some embodiments, the system is configured to de-identify the user input from the user before outputting to the third party health researcher.

The system and associated modules may further be configured according to any of the aspects and embodiments described herein.

BRIEF DESCRIPTION OF THE DRAWINGS

FIG. 12A-12I are example screens pertaining to an activity task module accommodated within the application framework, in accordance with certain embodiments.

DETAILED DESCRIPTION OF THE INVENTION

Figure 1:
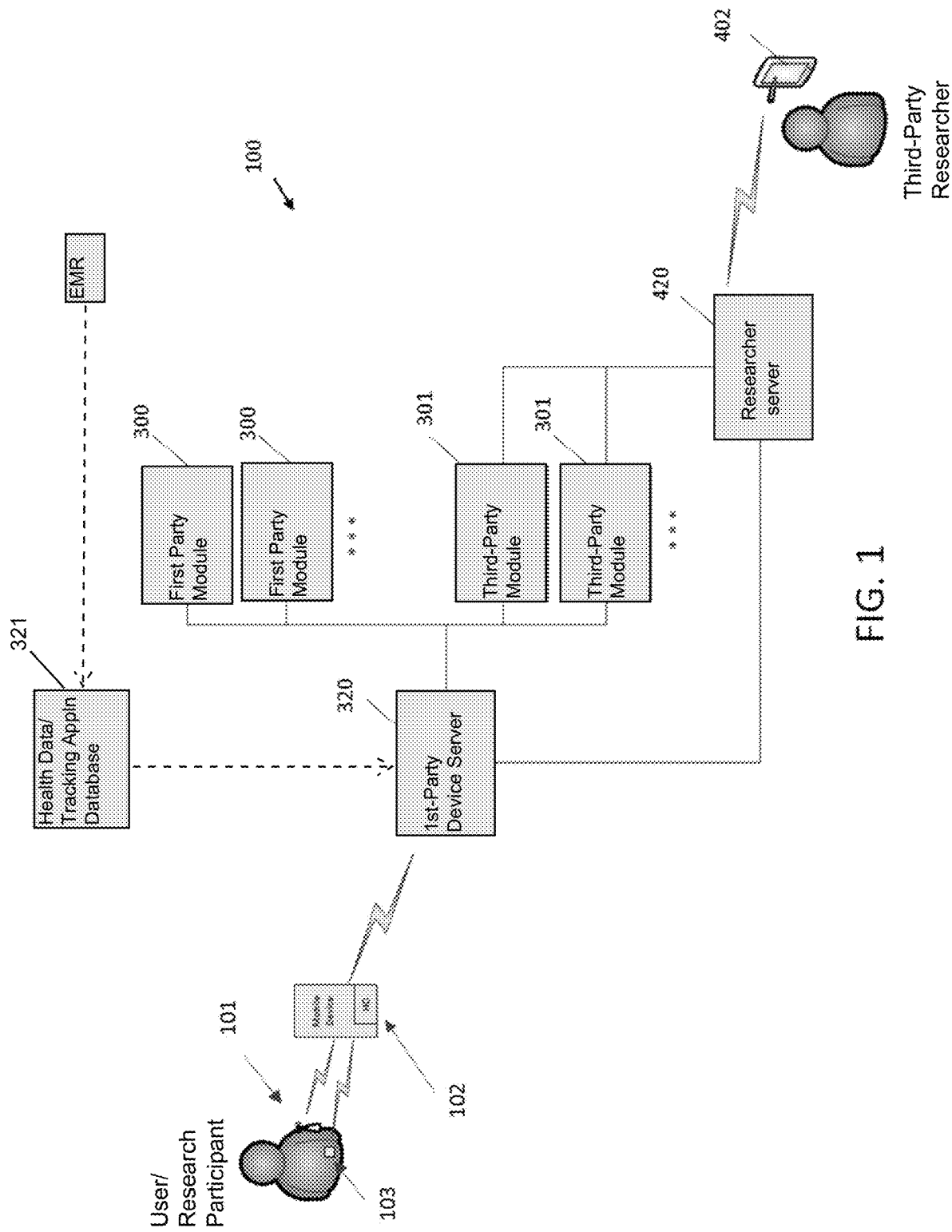
FIG. 1 is a simplified block diagram illustrating a system for facilitating research in accordance with certain embodiments of the present invention.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified so as not to obscure the example being described.

Embodiments of the present disclosure provide improved methods and systems for facilitating health research by improved communication between researchers and research participants through an application framework on a portable computing device of the participant. In one aspect, the application framework accommodates various differing types of modules that can be selectively used as needed for a particular research study to present and/or obtain health information to or from the research participant. In one aspect, the application framework is developed by a first-party and may include one or more modules developed by the first-party that can be utilized by a third-party researcher to present and/or obtain health information from the participant as desired. In another aspect, the application framework accommodates modules developed by a third-party, such as a researcher conducting the study, so that the presentation of information to the research participant can be customized according to the researcher's needs.

In one aspect, the application framework is configured to utilize health information accessible by the portable computing device (e.g. smartphone, tablet). Such health information may include: health information from the participants electronic medical record (EMR) accessed through a server communicatively coupled with the first portable device, or health information on a database, which may include health information entered by the user or obtained by the user (e.g., personal information collected by one or more wearable sensor devices and/or stored in a portable electronic device of the user). This aspect is advantageous as it allows the research to utilize a considerable amount of information that would likely be too burdensome to obtain with conventional methods. In certain aspects, the system is configured to segregate health information of the user such that the researchers may only access health information that the user has authorized release of or has intentionally included in information to be released for research. In certain other aspects, the health information may undergo de-identification such that the health information may be used for research without being associated with any particular user. This aspect may allow for release of health information that a user would otherwise be reluctant or averse to releasing for use in research.

In one aspect, the system may be implemented as a computing device configured with a memory and a processor. The processor may be configured to execute instructions stored on the memory to run the first-party application framework and to receive one or more modules from a third-party researcher in order to present research study information to a user, recruit the participant for the research study, obtain informed consent from the participant, as well as conduct surveys and obtain information regarding various tasks pertinent to the research study. The first-party application framework may also utilize one or more modules developed by the first-party in accordance with certain requirements selected by the third-party researcher.

Embodiments of the present disclosure are directed to, among other things, managing personal information received from external sources, or from other peripheral devices of a user. In some examples, the information collected by the data collection devices may be provided to a user device of the user (e.g., a mobile phone, a tablet computer, a laptop computer, a wearable computing device, etc.) and/or one or more first-party or third-party applications of the user device, before being selectively transmitted to a researcher for a treatment. In some examples, a first-party application may be one that is provided with the operating system (O/S) of the user device, is configured to operate natively with the user device, provided by the developers of the O/S for use with the user device, and/or trusted by the O/S and/or device. A third-party application may be one that is provided by a third-party or entity other than the developer/manufacturer of the user device and/or it's O/S. Examples of information being collected and/or managed may be health, fitness, and/or activity information of the user (e.g., blood glucose levels, weight, height, calories burned, heart rate, etc.). The user information may be categorized or otherwise identified by one or more data types (or categories). Weight, number of steps walked, number of calories burned, heart rate, etc., are each an example of such health data. Other data types (e.g., outside of health information) are also envisioned including, but not limited to, hours worked, hourly rate, miles per hour, pages read per minute, etc. A user device of the researcher allows for ready selection of a set of data of health information relevant to treatment and/or diagnosis, while the user device of the user determines a subset of the requested data set authorized by the user to be sent to the researcher.

In some embodiments, a first-party application framework may be executed on a user device of the user that is configured to receive, store, manage, and/or provide such user information to a service provider, to third-party applications, to other first-party applications, and/or to local storage of the user device. As part of the first-party framework, a first-party process may be executed by processors of the user device. The first-party process may include, but is not limited to, a daemon or other background process configured to communicate with the third-party applications, the O/S of the user device, and/or electronic storage of the user device. In some instances, first-party process may be configured to manage a data interchange for sharing some user data with third-party applications as well as the researcher. In this way, the first-party process may allow the researcher to access user information that was initially provided by the third-party application, a first-party application, or other third-party applications. Since health information of a user may be considered extremely personal and/or confidential, the user is provided with the ability to protect or otherwise not share some of the heath information with the researcher or certain researchers. In some examples, each third-party application may be instructed to request authorization for accessing particular (or all) data from the data interchange before transmitting the requested health information to the researcher.

I. System Overview

FIG. 1 illustrates a simplified diagram of a health research facilitating system 100 with enhanced exchange of health information, in accordance with embodiments of the present invention. The system 100 includes a portable electronic computing device 102 (e.g. smartphone, tablet, laptop, computer) associated with the user through which the user or a caretaker of the user (e.g. parent, nurse) can initiate a research related session with the researcher as well as communicate health information to a first researcher, typically to an electronic user device associated with the researcher (e.g. smartphone, tablet). In one aspect, the portable or user device 102 of the user typically includes a plurality of health data elements stored on a memory of the device or on a user data server 320 (e.g. server, cloud) accessible to the first portable computing device 102. Health information of the user is received in the user device 102, either input by the user or acquired from one or more sensor devices, such as a wearable sensor device 101 (e.g. sensor watch) or a specialized auxiliary sensor device 103 (e.g. heart monitor patch, ECG, blood glucose sensor, etc.). The health information is then wirelessly transmitted to a data server 320, typically a server associated with an application on the portable computing device 102 that facilitated collection of the health data (e.g. $1^{st}$ Party server supporting a $1^{st}$ Party Health Data Application on the portable computing device). In some cases, where the application developer is the same as the entity supporting general operation of the phone, the device server and the application server may be the same server.

In this system, the portable computing device 102 includes an Application Framework configured to interface with the user according to various differing modules. In one aspect, the Application Framework defines the manner and form in which the application interfaces with the user, for example the manner in which information is displayed to the user on the user interface of the portable computing device 102 as well as the manner in which the user manages the info (e.g. scrolls through the screens of information, advances to the next screen, or selects an option displayed on the screen), as well as how the information appears. In another aspect, the Application Framework is configured to interface with one or more sensor devices 101, 103 communicatively coupled with the portable computing device 102, for example, to control aspects of the user interface in accordance with outputs of the sensor and/or to monitor sensor data from the one or more sensors based on a user input so as to allow the portable device 102 to perform various functions relating to the research study, including but not limited to: initial communication of the research study, recruitment of research participants, consent of research participants, acquisition of health information for use in health research, communication of follow-up information/inquiries as needed, and various other research related tasks. While the Application Framework provides the frame or means by which these tasks are accomplished using the portable computing device, the content and particular requirements unique to each task are informed by one or more module received by the device 102.

In this system, the modules may be $1^{st}$-party Modules 300 or $3^{rd}$-party Modules 301. The $1^{st}$-Party Modules 300 are developed and provided by the same entity that developed and provided the Application Framework and may be provided along with the Application Framework or made available through the device server for use on the device as needed. The $3^{rd}$-party 3 party modules are developed and provided by $3^{rd}$-party entities, such as a $3^{rd}$-party researcher, and include various content/elements that may be unique to the particular research study being conducted and not readily available through the $1^{st}$-party modules 300. In one aspect, the 3rd-party modules may be developed by the $3^{rd}$-party researches using a portable device 402 (e.g. tablet, laptop, computer) associated with the researcher. The portable device 402 of the researcher may include an application corresponding to Application Framework that allows the researcher to enter the requirement content or information within a module so as to suitable for use with the Application Framework. The $3^{rd}$-party modules 301 may be provided and stored on a third-party server 420 that is communicatively coupled to the $1^{st}$-party server of the Application Framework and/or the device server for access by the user device 102. The Application Framework is configured to provide the desired tasks based on either or both of the $1^{st}$-party and $3^{rd}$-party 3 party modules received. In one aspect, the Application Framework may utilize both a 1st-party and 3rd-party module received to inform a single action or task communicated to the user. It is appreciated, however, that a research study could be conducted using solely 1st-party 3rd-party modules 300 or solely 3 party modules 301 as appropriate for the health study being conducted.

In another aspect, the 1st-party server 320 is communicatively coupled with or includes a health information database 321 associated with the user. The health information database 321 stores or accesses a plurality of health elements acquired through a Health Data Tracking Application stored on the user device 102. The plurality of health data elements may be used by various entities such as regulated medical service providers that may utilize the acquired health information received from the user data server and perform additional health related services, such as processing health data to determine trends or various other health metrics. Such processed data is generally made available to the user device 102 through the user data server 320.

In one aspect, the research server 420, as well as any researcher electronic device 402, is communicatively coupled 1st-party server 320 which in turn may be coupled with the electronic medical record (EMR). This aspect allows health information from the EMR to be obtained, as needed, along with any health information or input from the user device and de-identified from the user before transmission to the research server 420, which safeguards privacy of the user's medical records. Since the user device 102 of the user is communicatively coupled to the research server 420 through the Application Framework, research related sessions can be conducted remotely without requiring the user to visit the clinic and large amounts of health information can be rapidly transmitted while still safeguarding user privacy. This approach is advantageous over conventional methods of conducting research as it reduces the burden on the user/research participant to supply any health data directly to the researcher. In addition, in some studies, this allows the user to be recruited and enrolled without any in-person contact or periodic visits to a research facility, which would likely discourage some users from participating in a research study, particularly for those research studies relating to sensitive or controversial topics.

In one aspect, user devices 102 in combination with the one or more sensor devices, in this example, wearable device 101 and/or auxiliary sensor device 103, allow collection and/or analysis of large amounts of health data for use in medical research in amounts far greater amounts than conventional research techniques could reasonably attain. Dealing with such large amounts of data, however, may negate any associated benefits such information provides as it may prove difficult and overly time consuming to manage using conventional methods of data collection in health research. In one aspect, the Application Framework is configured to output only health data information that is authorized for disclosure to the researchers. Typically, when accessing health information obtained outside of the Application Framework, such as from the health information database 321 or EMR, the permissions and authorizations are determined and/or set by the user in the other applications associated with collection or access of that health data.

In some embodiments, health information may be input directly into the user device 102 by the user or may be obtained through one or more health information acquisition devices or sensors, such as wearable device 101 (e.g. watch, wristband) that the user wears such that one or more sensors of the wearable device measure one or more parameters that can be used to determine health data, either directly or indirectly. For example, the wearable device 101 may measure body temperature directly or may measure activity levels by use of one or more accelerators. In some embodiments, the wearable device 101 is incorporated within the first-party framework of the user device 102. The one or more sensor devices may be specialized for sensing and/or measuring various health metrics, including but not limited to activity level, activity tracking, respiration, body temperature, heart wellness data, hydration levels, perspiration, blood glucose, salinity, sleep cycles, posture, $O_2$ levels, muscle engagement, or any combination thereof. The collected data may or may not be specific to the condition being analyzed in the study and may be collected without requiring any additional input from the user to initiate collection of the sensed data. In some embodiments, the sensed data is collected over a duration of time, the duration generally exceeding a few days, such one or more weeks, months or years. Typically, these auxiliary health sensor devices 103 are third-party devices that are supported by a third-party application and managed by used of a third-party service provider 300. Such sensors 103 may also be a regulated medical device that is supported through a regulated medical service provider 301. The user device 102 communicates the health information to the user data server 320, which may be selectively accessed by the researcher data system based on identification of a subset of data authorized by the user to be released by the researcher.

Figure 2A:
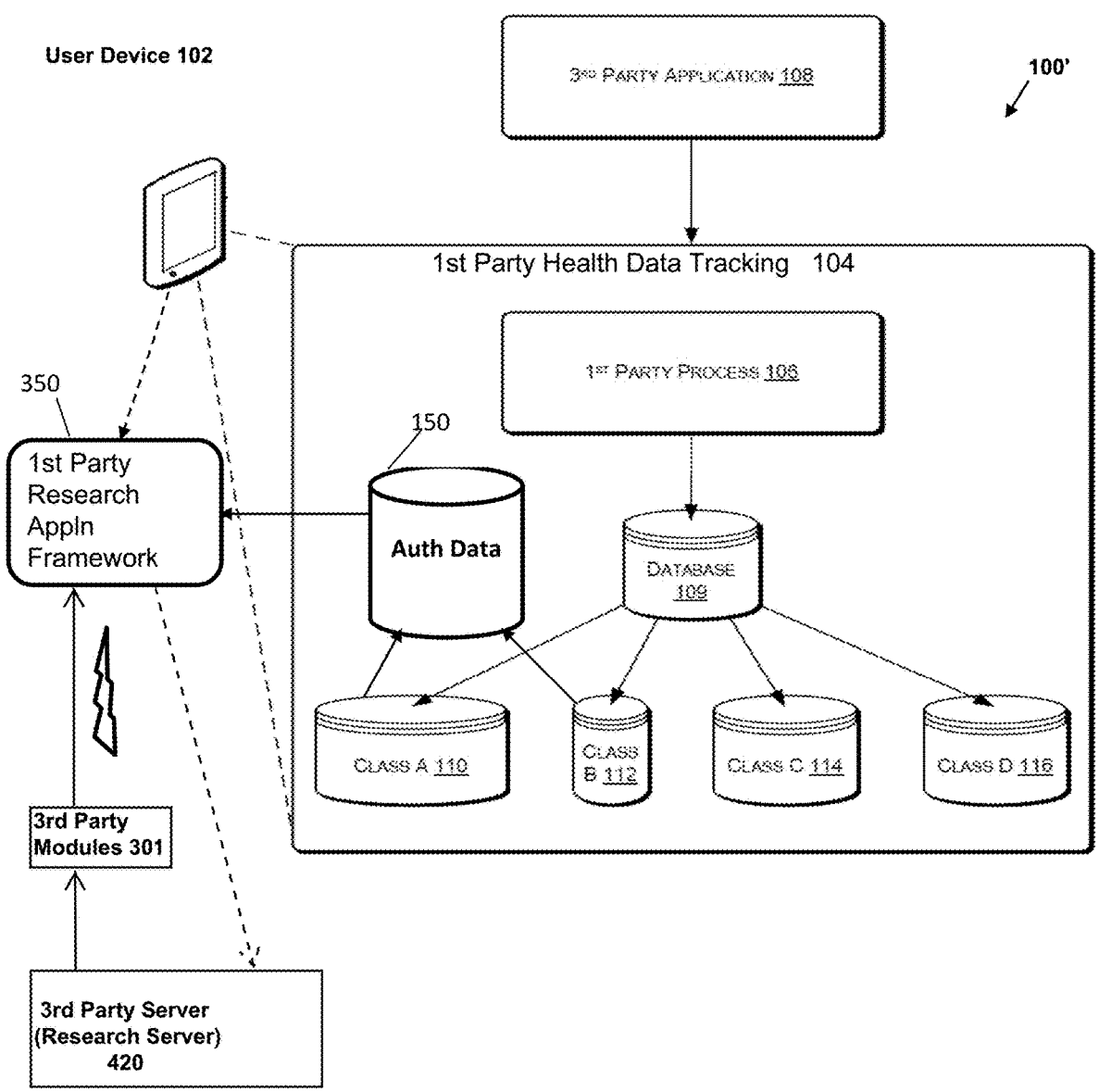
FIG. 2A is a simplified block diagram illustrating an example system architecture for facilitating health research as described herein, in accordance with certain embodiments.

FIG. 2A illustrates a simplified architecture diagram 100' depicting a user device 102 configured to implement a first-party Health Data Tracking Application 104 that manages exchange of health information received by the user device 102. The first-party application 104 may be configured as an application framework for managing user data of a plurality of data collection devices. In some examples, because the first-party application manager 104 is provided or otherwise controlled by developers of the user device 102 and/or its associated O/S, the first-party application manager 104 may be considered a trusted framework with full access to all user data. The Research Application Framework 350 is yet another framework stored on the user device 102 that manages the health information obtained through effecting the research modules (e.g. the 3rd-party modules 301 received from the research server 420. In one aspect, while the manager 104 (also known as the framework for Health Data Tracking) may only allow a portion of its health data to be shared within the Research Application framework, in general, any sensor data of health information obtained through the Research Application Framework is automatically uploaded to the Health Data Tracking 104.

In some examples, the first-party process 106 may be configured to manage (e.g., store, retrieve, encrypt, etc.) user data via a database 109 of the user device 102. As part of the first-party application manager 104, the database 109 may be divided or otherwise logically separated into a plurality of classes of data stores. For example, the user data may be stored in at least one of a class A data store 110, a class B data store 112, a class C data store 114, and/or a class D data store. In some examples, the class A data store 110 may be configured to store personally identifiable user information (e.g., personal health, fitness, or activity data). In some examples, this data is only available to the third-party application 108 when the user device 102 is unlocked. By way of example, the user device 102 may be unlocked when the user associated with the user device 102 has correctly entered his or her user identifier (ID) and password (e.g., when logging in and/or unlocking the lock screen). Class B data store 112 may be configured to store "journal" type data. Journal data may include, but is not limited to, personally identifiable user information and/or other metrics associated with use of one or more data collection devices and/or the third-party application 108. When the user device 102 is locked, the journal data of the class B data store 112 may be inaccessible to the third-party application 108. However, in some examples, data from a data collection device or an application (e.g., the third-party application 108) may be read from or written to the class B data store 112 by the first-party process 106 while the device is locked as long as the first-party process 106 is active. If, however, the first-party process 106 fails or otherwise becomes inactive in the process of reading or writing data to the class B data store 112, the data may become permanently inaccessible, and new data may not be written to the class B data store 112 until the first-party process 106 and/or a new session of the third-party application 108 have relaunched. In this way, the data of the class B data store remains securely accessible because it is only accessible to the first-party process 106 while receiving data from a third-party application 108 during the active session, and no other applications can read that data.

In some aspects, the class C data store 114 may be configured to store metadata associated with the management of the user health, fitness, and/or activity data. This metadata, in some cases, may only be accessible after the first unlock of the user device 102. As such, if the user device 102 reboots (based at least in part on a software issue or a loss of battery power), this data may not be available until the user unlocks at least once. In some aspects, this may prevent jailbreaking or other hacking techniques from accessing this data. The metadata stored in the class C data store 114 may include subscription information, access permission information, and/or safe metadata, but may not, in some examples, identify or be directly associated with any health information (e.g., the data stored in the class A data store 110). The class D data store 116 may be configured to store free-form (e.g., unstructured) information provided by the user. In some examples, this may be health data; however, it may not be updatable and/or linked to any third-party applications (e.g., the third-party application 108) or data collection devices. The class D data may always be available to the first-party process 106 and/or the third-party application 108. In some aspects, the class D data may be pre-filled using information from the third-party application 108 and/or one or more other applications or processes. However, the user may be able to enter additional data, update the data, include incorrect data, or otherwise configure the information in the class D data store 116 as they see fit. The class D data may be available on the lock screen of the user device 102 without anyone (e.g., the user) logging in or otherwise unlocking the user device 102. In this way, the lock screen or another accessible screen of the user device 102 may be analogous to a medical ID bracelet. In some cases, an emergency icon or other function on the lock screen may enable the presentation or rendering of the class D data upon request for anyone (e.g., an emergency medical technician or the like) to see. Further, in some aspects, the third-party application 108 may not have access to the class D data, in part because it may be unstructured data that would be difficult for the third-party application 108 to process.

In one aspect, the first-party process 106 identifies health information data authorized by the user to be sent to the researcher as Authorized Data 150. Such an identification may be based on a default, a pre-selection or a live input from the user in response to a query. Typically, the most common types of information being requested and identified as Authorized Data would be Class A and Class B types of information. Some embodiments may include release of various other types of data, for example to allow further processing of collected data by an application on the researcher device. While Authorized Data 150 is shown schematically as a separate element, it is appreciated that such authorized data is not required to be stored in a separate location, nor is it required to be identified before the request for information is made. This may instead be accomplished in various different ways, for example, by tagging or using a specific identifier for each field of data to denote which data items are authorized for release by the user and to which parties the data is authorized for release. In some embodiments, the identification of authorized data is determined only after receiving a request for data. In systems having exceedingly large amounts of health information data, this approach may be more efficient, since the data is only analyzed to determine authorization of the data set that is being requested.

As shown in FIG. 2A, communication of data between the user device 102 and the researcher device 302 may be facilitated by use of an application common to both devices, such as the Researcher Connect Application 350, 351 provided on the user device 102 and the researcher device 402, respectively, such as shown in System 100' of FIG. 2. In this aspect, the devices may communication through a common server (e.g. physical server or cloud) that supports the common application, as opposed to going through separate but interconnected server information. The researcher device may separately couple with the researcher server 420 as well as the EMR to import additional information external to the health information data associated with the mobile user device 102. While the application may be common to both devices, generally, the application would include features suited for the particular uses associated with each device. For example, the application may display health information data more succinctly on the user device, than on the researcher device. In addition, the application of the user device requires a feature that allows the user to select data authorizations, while the researcher device application requires a feature that allows the researcher to select sets of data to be requested.

In some embodiments, this application is a first-party application on each of the devices and may be incorporated partly or fully into the first-party framework. For example, the application may run in the background during normal operation of either device, so as to be readily responsive to a communication from either device using the application. By using a first-party application or platform for facilitating session initiation and communication regarding researcher health information request and release of authorized data by the user, the system allows a central location from which the user can manage and authorize release of data that may be provided by various different sources (e.g. third-party application, third-party servers). While these different sources and third-party applications/servers may each include their own permission and authorizations regarding storage and transmittal of secure health information data, routing the transfer of data through the first-party application ensures that the user is aware exactly what data is being released and allows the user an opportunity to change authorizations of data and release data, regardless of permissions associated with the third-party application or other data source.

Figure 2B:
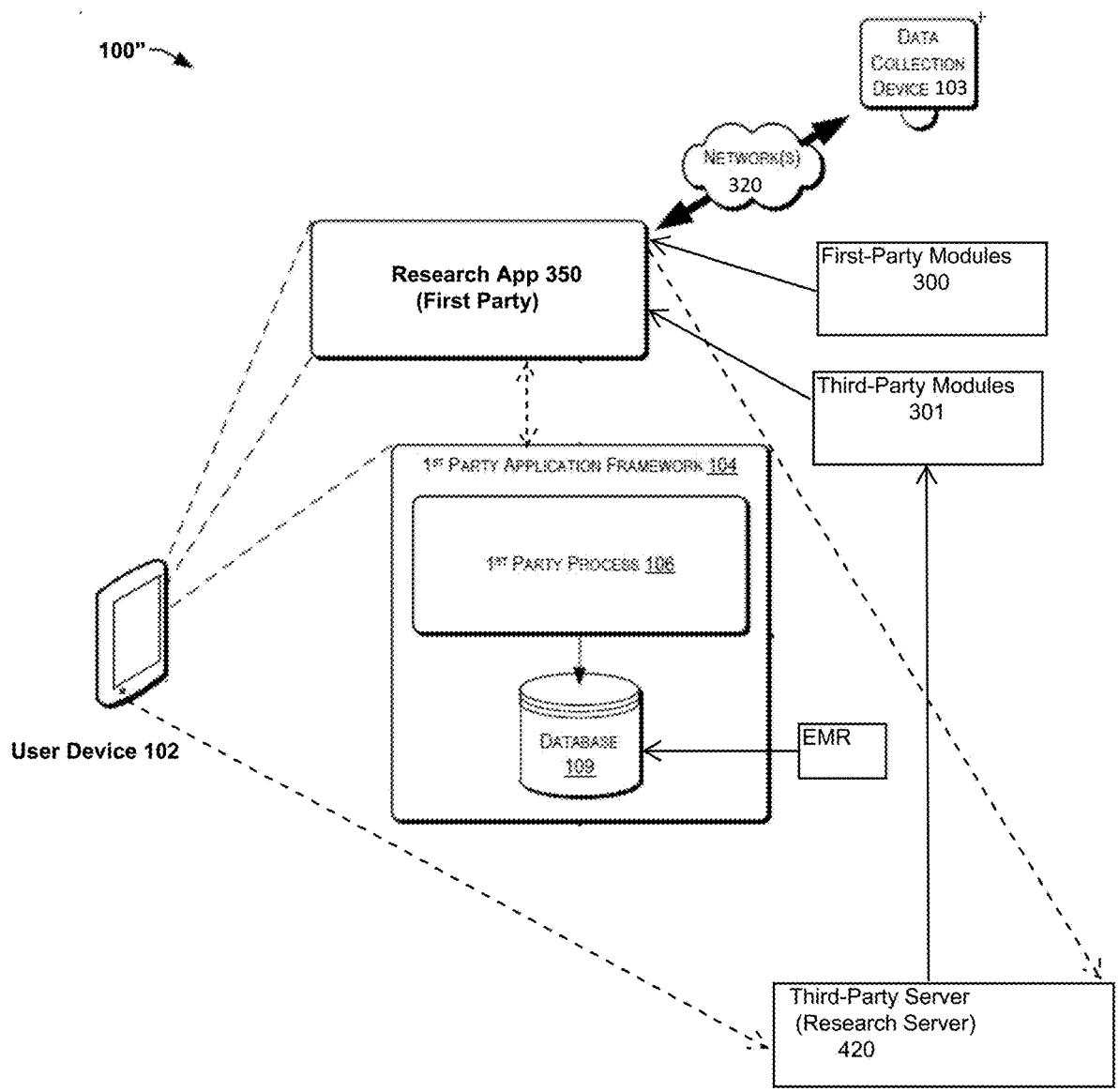
FIG. 2B is a simplified block diagram illustrating an example system architecture for facilitating health research as described herein, in accordance with certain embodiments.

FIG. 2B illustrates another example system 800 using a user device 102 and associated health information collection scheme in accordance with the present invention. FIG. 2B depicts a user device 102, the first-party application framework 104 for health data tracking, and the first-party process 106 of FIG. 2A. In some examples, one or more third party applications (e.g., third-party source application 802 and/or third-party application 804) may be in communication with the first-party application manager 104 and/or the first-party process 106 for providing user information collected by a health data collection device 101. In some examples, the data collection device 103 may be any wearable or specialized user device configured to collect activity, health, medical, and/or fitness information about a user. This information may then be provided to one of the third-party applications (e.g., the third-party source application 303 in this example) via one or more networks. Once received by the third-party source application 303, the information can be provided to the first-party process 106 for storage in the database 109.

As noted above, the user device 102 may be configured to manage a data interchange for reading and/or writing user data to the database 109, and for sharing that user data among one or more authorized third-party applications. In some examples, the data collection device 302 may be configured to provide health, fitness, activity, and/or medical data of the user to a third- or first-party application (or process). In turn, this data may be shared, aggregated, and/or accessed via the first-party Health Data Tracking manager 104 that may be configured to implement the first-party Health Data Tracking manage 104. The user device 102 may be any type of computing device such as, but not limited to, a mobile phone, a smartphone, a personal digital assistant (PDA), a personal computer (e.g., laptop or desktop), a thin-client device, a tablet computer, an electronic book (e-book) reader, a wearable device, etc. In some examples, the user device 102 may be in communication with the service provider computers 304 and/or the data collection device via the networks shown or via other network connections.

In one illustrative configuration, the user device 102 may include at least one memory and one or more processing units (or processor(s)). The processor(s) may be implemented as appropriate in hardware, software (e.g., computer-executable instructions, firmware, etc.), or combinations thereof. Computer-executable instruction or firmware implementations of the processor(s) may include machine-executable instructions written in any suitable programming language to perform the various functions described. The user device 102 may also include geo-location devices (e.g., a global positioning system (GPS) device or the like) for providing and/or recording geographic location information associated with the user device 102. The memory may store program instructions that are loadable and executable on the processor(s), as well as data generated during the execution of these programs. Depending on the configuration and type of user device 102, the memory may be volatile (e.g., random access memory (RAM)) and/or non-volatile (e.g., read-only memory (ROM), flash memory, etc.). The user device 102 may also include additional removable storage and/or non-removable storage including, but not limited to, magnetic storage, optical disks, etc. The disk drives and their associated non-transitory computer-readable media may provide non-volatile storage of computer-readable instructions, program modules, data structures, and other data for the computing devices. In some implementations, the memory may include multiple different types of memory, such as RAM, static random access memory (SRAM), dynamic random access memory (DRAM), or ROM. While the volatile memory described herein may be referred to as RAM, any volatile memory (e.g., that does not maintain data stored therein once unplugged from a host and/or power) would be appropriate.

Additional types of computer storage media that may be present in the user device 102 may include, but are not limited to, phase-change RAM (PRAM), SRAM, electrically erasable programmable read-only memory (EEPROM), flash memory, compact disc read-only memory (CD-ROM), digital video disc (DVD), magnetic cassettes or tape, magnetic disk storage, or any other medium that can be used to store the desired information and that can be accessed by the user device 102. Combinations of any of the above should also be included within the scope of non-transitory computer-readable media. Alternatively, computer-readable communication media may include computer-readable instructions, program modules, or other data transmitted within a data signal, such as a carrier wave, or other transmission. However, as used herein, computer-readable storage media does not include computer-readable communication media. The user device 102 may also contain communications connection(s) that allow the user device 102 to communicate with a data store (e.g., the database 109), or another computing device via one or more networks. The user device 102 may also include I/O device(s), such as a keyboard, a mouse, a pen, a voice input device, a touch input device, a display, speakers, etc.

Turning to the contents of the memory in more detail, the memory may include an operating system and/or one or more application programs or services for implementing the features disclosed herein. The background module 336 may be configured to launch and/or relaunch third-party applications in as background process. In some examples, the background module 336 may also be configured to verify that the third-party application has finished processing the data it requested, by continuing to relaunch the third-party application in the background until notification is received that the third-party application has completed processing. An extension module may be configured to handle registering new data types with the first-party framework module in order to extend the functionality of the first-party application manager 104 of the systems shown in FIGS. 2A-2B. Further, the aggregation module may be configured to aggregate or otherwise combine (and, in some examples, provide presentation for) user data received from multiple different data sources. The service provider computers may also be any type of computing device such as, but not limited to, a mobile phone, a smartphone, a PDA, a personal computer, a thin-client device, a tablet computer, an e-book reader, a wearable device, etc. In some examples, the service provider computers 304 may be in communication with the user device 102 and/or the data collection device 302 via one or more networks or via other network connections.

Figure 3:
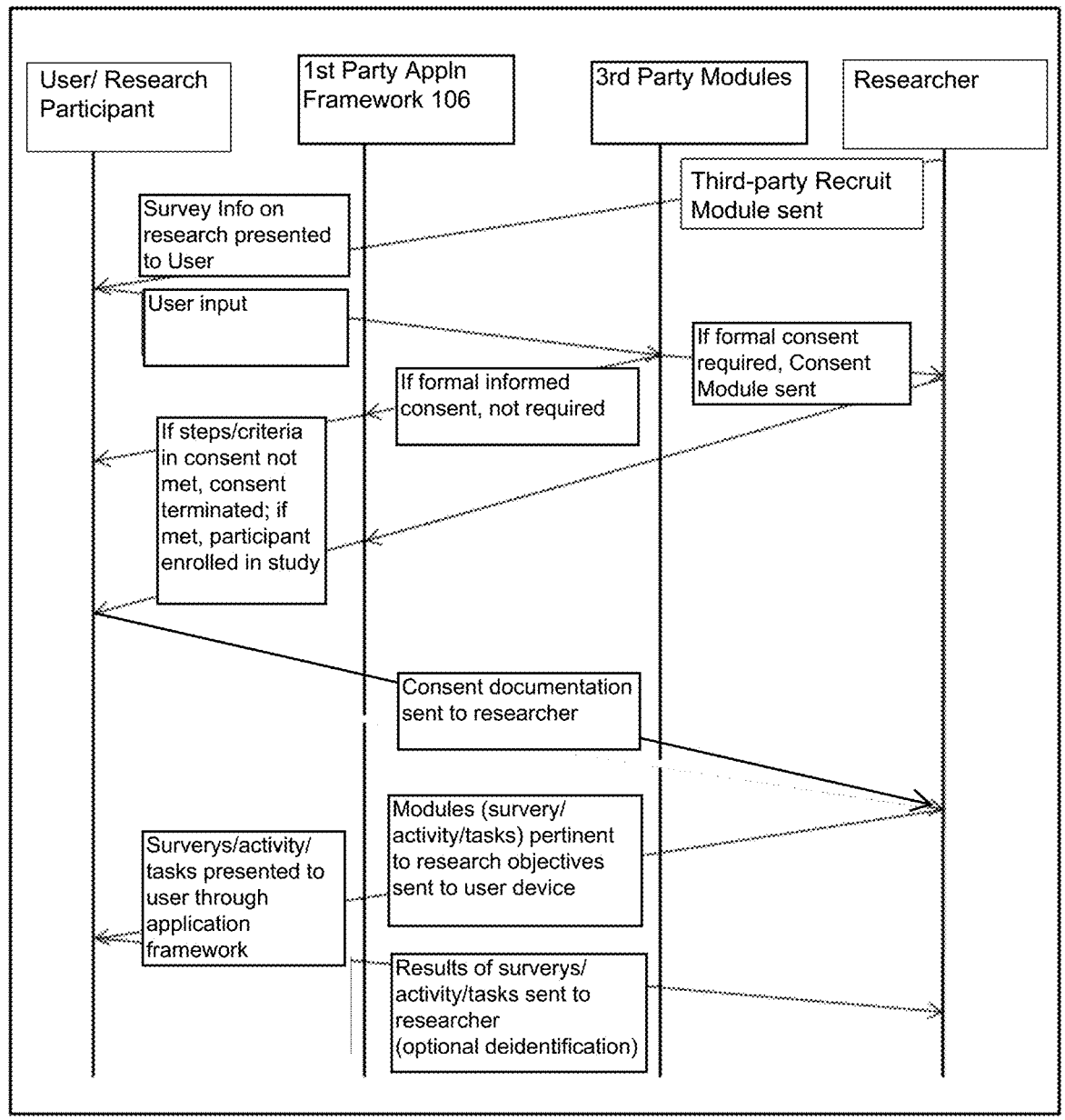
FIG. 3 is a sequence diagram illustrating various system features to facilitate research a third-party researcher and a research participant using a portable device of the participant, in accordance with certain embodiments.

FIG. 3 illustrates an example sequence diagram describing features of the research facilitating system during simulated research conducted in accordance with the invention. In one aspect, the researcher and user/research participant's communication is facilitated by the $2^{nd}$ party application framework on the user device and one or more modules, such as the $3^{rd}$ party modules from the researcher. First, the researcher provides information describing the research study for purposes of recruiting participants by sending a Recruitment Module. Alternatively, such information could be accessed by the user device through the Application Framework from a database. The research study can be presented to the user on a graphical user interface display screen as an advert based on one or more attributes of the user (or based on health information data of the user stored on the user device), or the study can be presented to the user in response to a user input request for a list of research studies available. In response to a user input indicating interest in participating in a research study, if formal written informed consent is required, the research send a Consent Module with the information/steps/criteria needed to obtain informed consent. If certain criteria for consent are not met (e.g. failure of comprehension test or response indicating lack of engagement), the consent process is ended. If the requirements for informed consent are met, then typically a consent form is displayed to the user and a signature requested, an image of which is then output to the researcher for purposed of record keeping. Once informed consent is obtained, the researcher may send any number of $3^{rd}$ party modules and/or select certain pre-defined $1^{st}$ party modules to elicit information from the user for the research study. The modules may be configured to provide instruction to the user in the form of information surveys having one or more questions, or activities and tasks that may use sensor data during performance of the activity or task to verify and/or analyze certain parameters relevant to the research study. Once the input is obtained from the user, in the form of user input (e.g. selection, entry of text or numeric) or in the form of input received from one or more sensor devices integrated with or external to the user device, the results are then sent back to the third-party researcher. In many such studies, the health information relating to performance of the modules undergoes de-identification so as to safeguard the privacy of the user.

Figure 4:
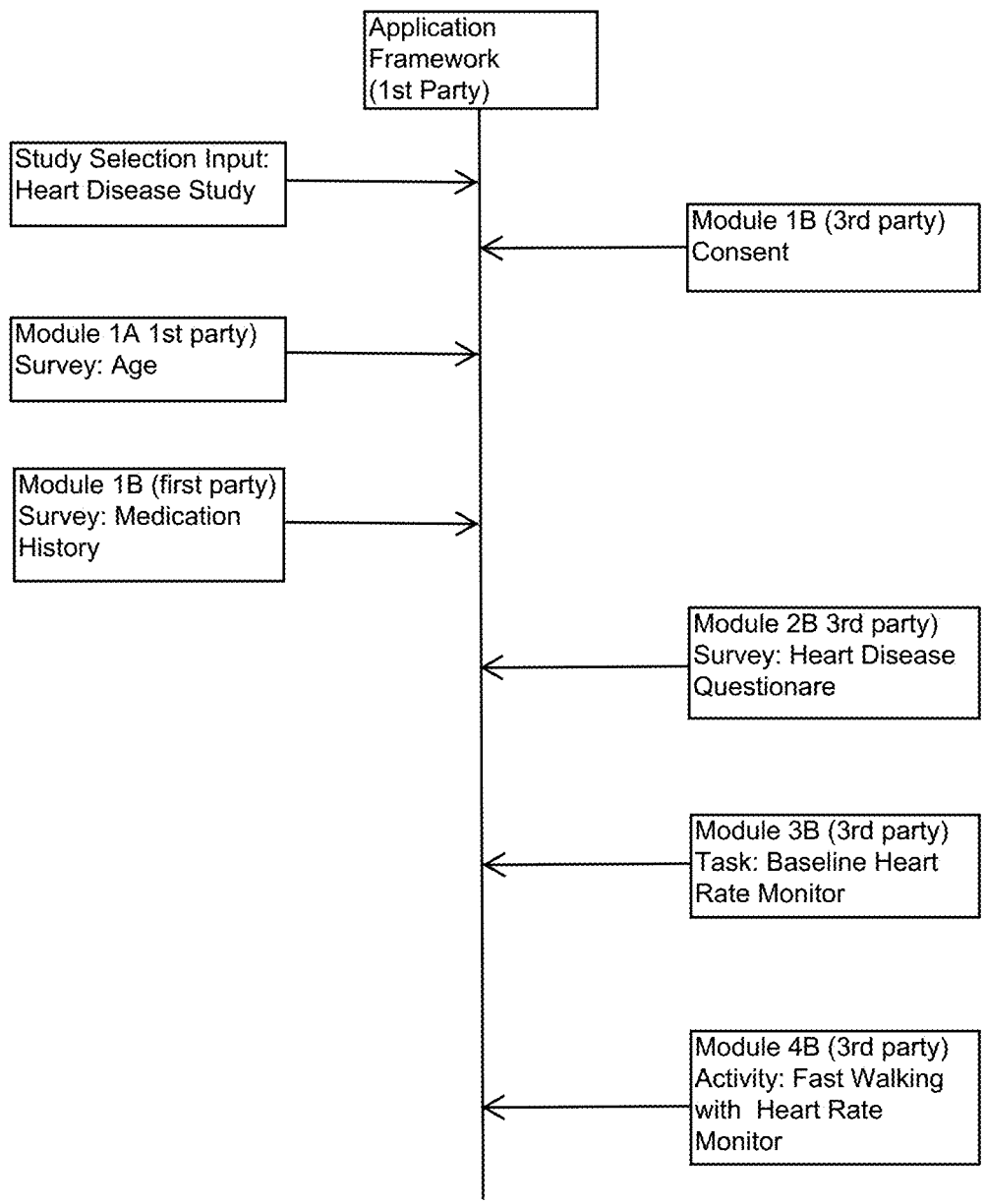
FIG. 4 is a schematic of the process by which a module incorporated into an application framework within a portable device of the research participant, in accordance with certain embodiments.

In the sequence schematic shown in the example of FIG. 4, the Application Framework is used with both $1^{st}$ party and $3^{rd}$ party modules to recruit a user in a heart disease study. First, the Application Framework receives a study selection input from the user selecting the heart disease study. In response, the researcher sends a third-party module (Consent Module 1B) to the Application Framework. The Consent module may include information specific to the study being undertaken and may further select one or more $1^{st}$-party modules to be used during the consent process, such as Survey Module 1A: Age and Survey Module 1B: Medication History. These surveys are pre-defined surveys having one or more questions that may be used as needed by the third-party. After consent is obtained and the participant is successfully enrolled in the health study, one or more additional modules are sent and/or identified to elicit health information relating to the study from the user, such as Survey Module 2B: Heart Disease Questionnaire, Task Module 3B: Baseline Heart Rate Monitor and Activity Module 4B: Fast Walking with Heart Rate Monitor. Each of these three modules are developed by the $3^{rd}$ party according to requirement unique to their particular study. Each of Task Module 3B and Activity Module 4B includes monitoring of sensor data to measure a parameter (e.g. heart rate, walking speed) for use in researching heart disease.

II. Example Module Types

Figure 5A:
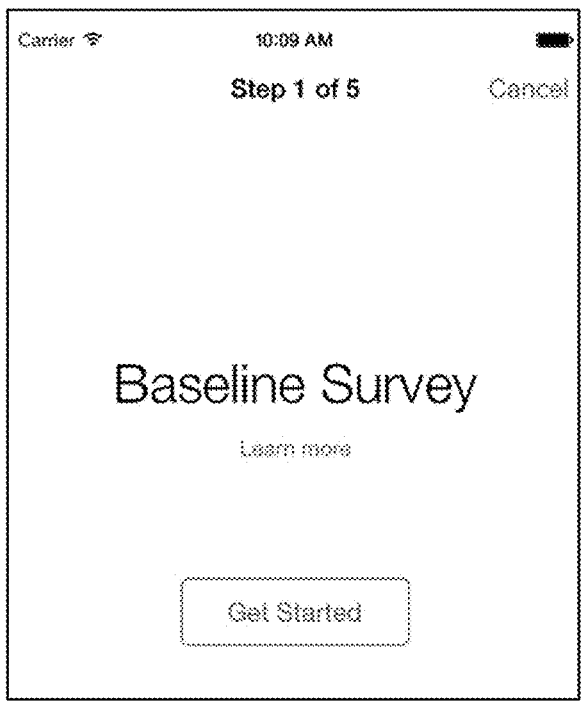
FIGS. 5A-5N are example screens displayed on the portable device of the research participant that pertain to differing types of modules accommodated by the application framework, in accordance with certain embodiments.

In order to further illustrate the different types of modules, reference is made to FIGS. 5A-5N, which depict screen displays pertaining to the different types of modules for use with the Application Framework described above. The different types of modules include, but are not limited to: Surveys, Instruction Step, Informed Consent, Active Tasks and Passive Data Collection. The use of each of these types of modules within an example Application Framework is described in further detail below:

A. Survey Modules

To use the survey module in Application Framework, one first instantiates a model object hierarchy describing the set of questions to be asked. The top level object in this hierarchy implements the RKTask protocol. Each logical piece of the task is a step (a subclass of RKStep). Tasks are presented using RKTaskViewController, which informs its delegate when results are produced. When the user completes a task, the survey results appear on the result property of the task view controller. The root task result has a step result for each step the user completed, and these may in turn have subsidiary results. For certain types of tasks, where large amounts of data are produced, the data may be stored on disk and the result object may simply provide a reference to that file. These results can be linked back to the step that produced them via the identifier. Every result records an identifier, the start and end timestamp for the collection of the result, and any data collected by the step. When a developer needs to make a task dynamic rather than just running through a predefined sequence, they can implement the RKTask protocol themselves.

In an example, using RKOrderedTask, a built-in implementation of RKTask, the developer might create a sequential task consisting of a series of questions. This would instantiate a survey with a single boolean question:

```
RKStep *introductionStep = [[RKInstructionStep alloc]
initWithIdentifier:@"introduction"];
introductionStep.title = @"Baseline Survey";
RKStep *booleanStep = [[RKQuestionStep alloc]
initWithIdentifier:@"baseline_medication"];
booleanStep.title = @"Do you take any diabetes medications?";
booleanStep.answerFormat = [RKBooleanAnswerFormat new];
booleanStep.optional = NO;
RKOrderedTask *task = [[RKOrderedTask alloc]
initWithIdentifier:@"baseline_task" steps:@[introductionStep,
booleanStep]];
```

To present this task, the developer hands it off RKTaskViewController for presentation:

```
RKTaskViewController *tvc = [[RKTaskViewController alloc]
initWithTask:task taskRunUUID:[NSUUID UUID]];
tvc.delegate = self;
[self presentViewController:tvc animated:YES completion:nil];
```

Figure 5B:
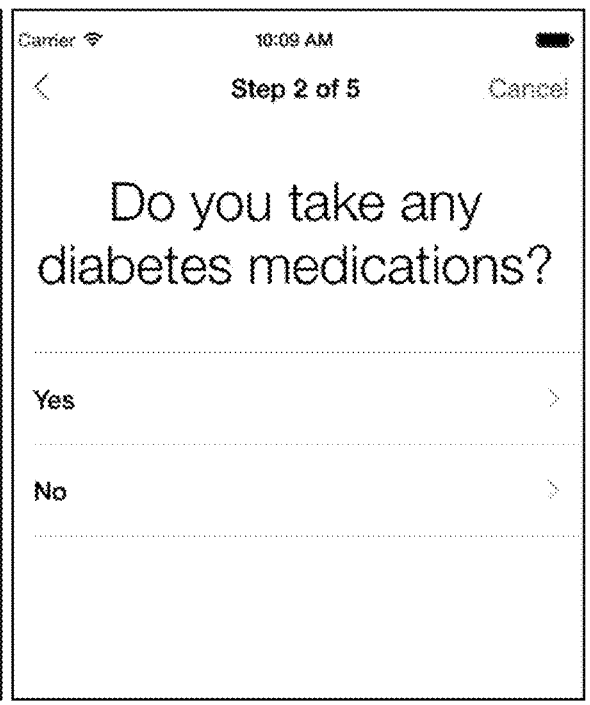
Figures 7A, 7B, 7C:
FIG. 7A-7C are example screens pertaining to additional examples of survey modules accommodated within the application framework, in accordance with certain embodiments.
Figure 8A:
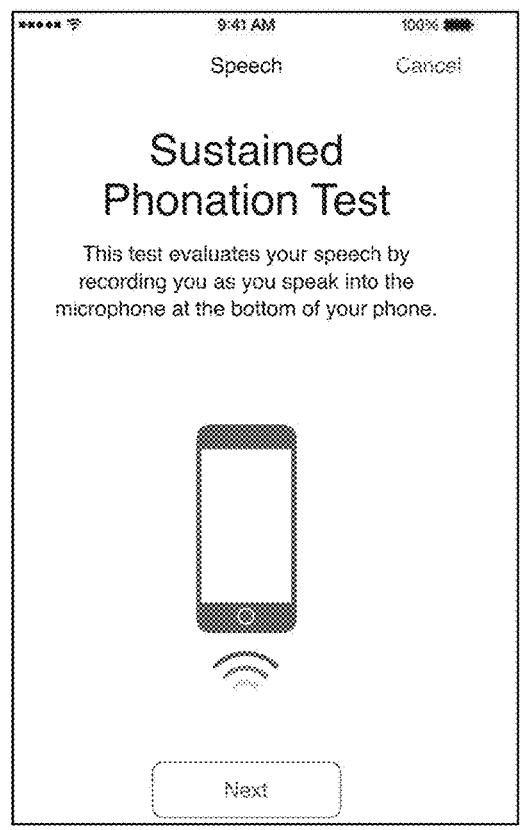
FIG. 8A-8F are example screens pertaining to an activity task module accommodated within the application framework, in accordance with certain embodiments.
Figure 8B:
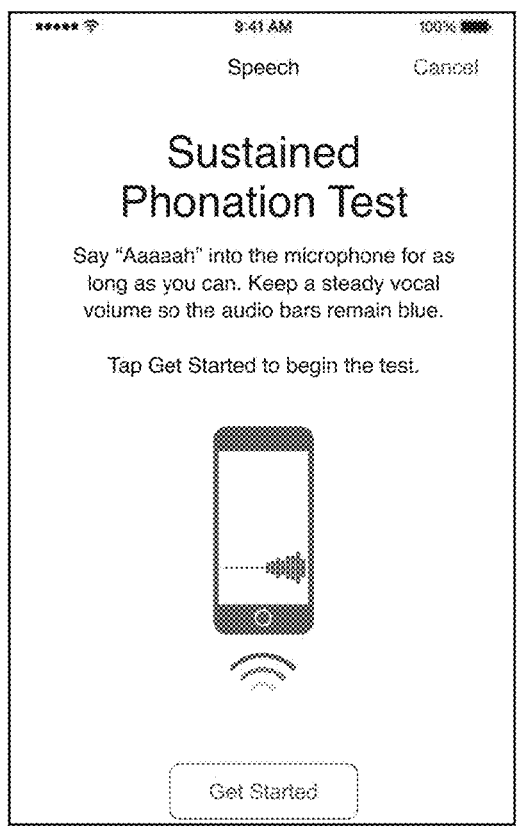
Figure 8C:
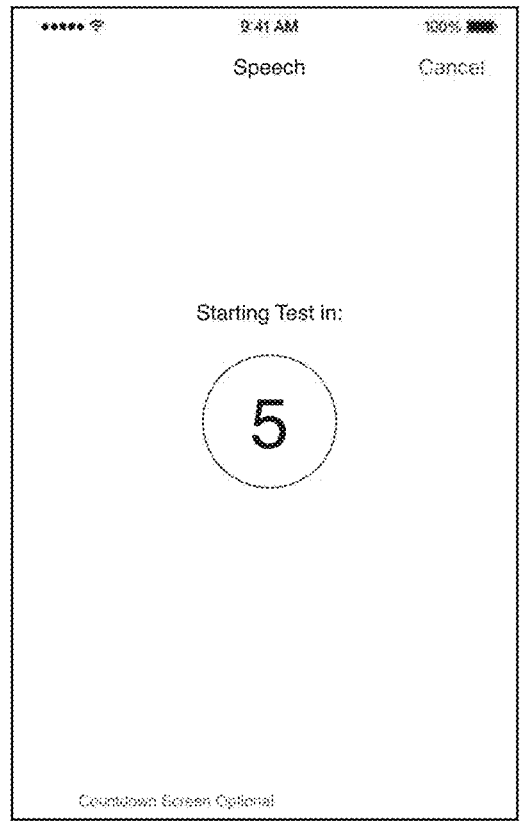
Figure 8D:
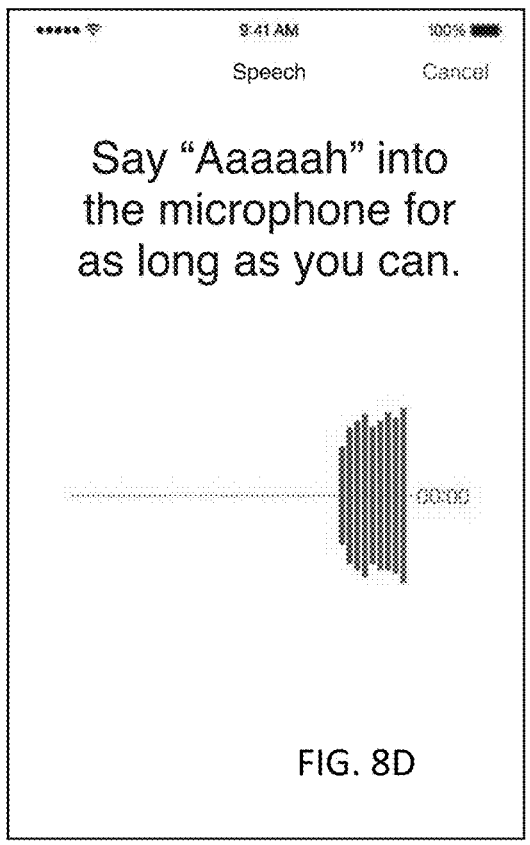
Figure 8E:
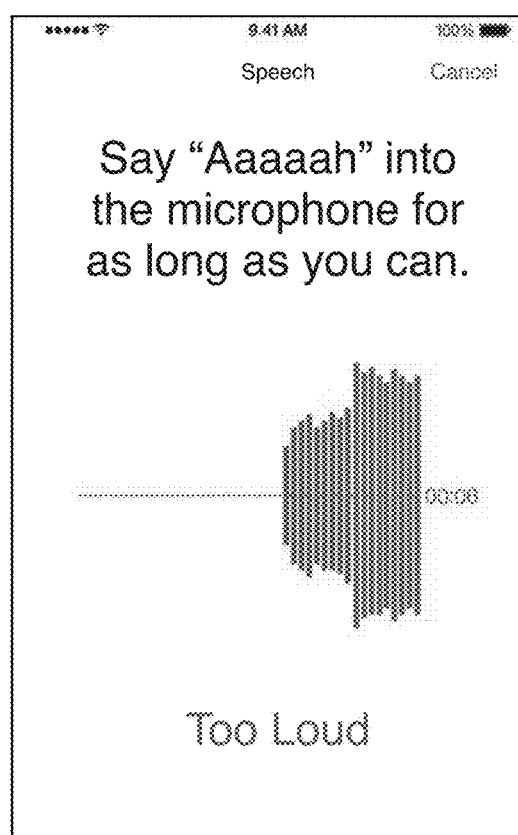
Figure 8F:
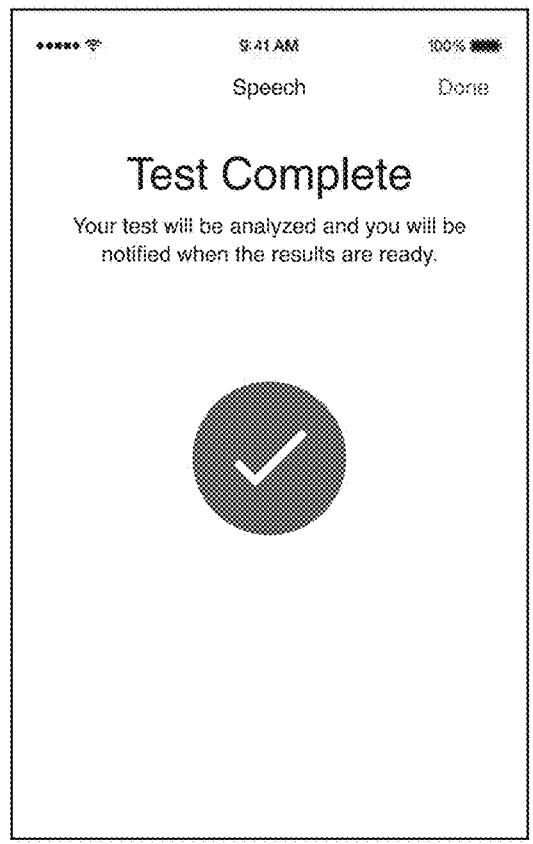
Figure 9A:
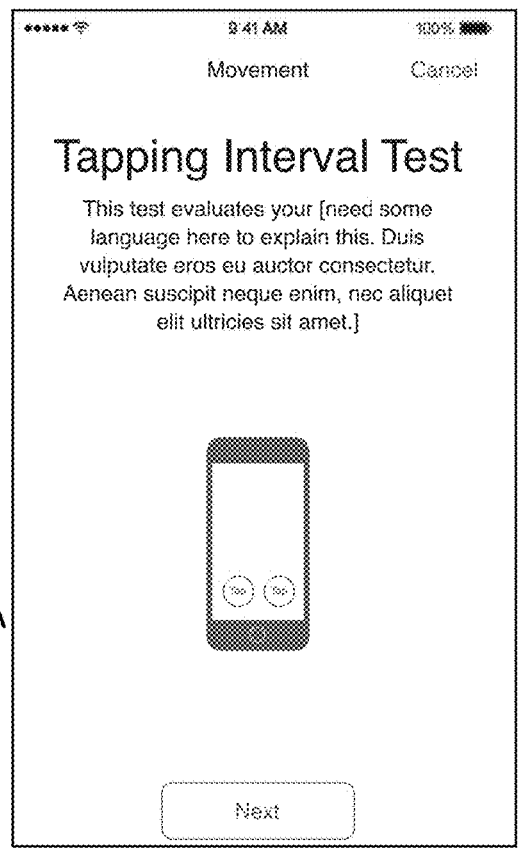
FIG. 9A-9G are example screens pertaining to an activity task module accommodated within the application framework, in accordance with certain embodiments.
Figure 9B:
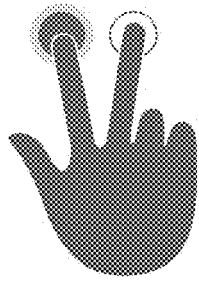
Figure 9C:
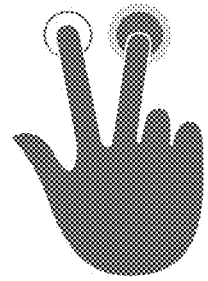
Figure 9D:
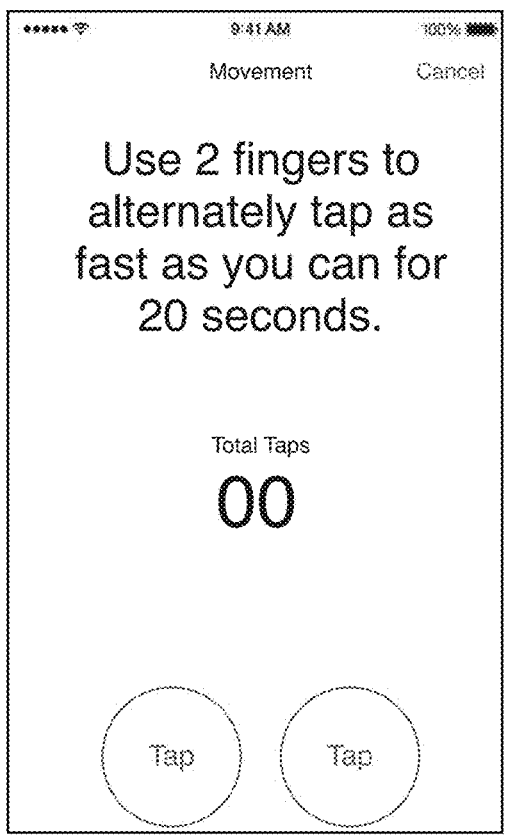
Figure 9E:
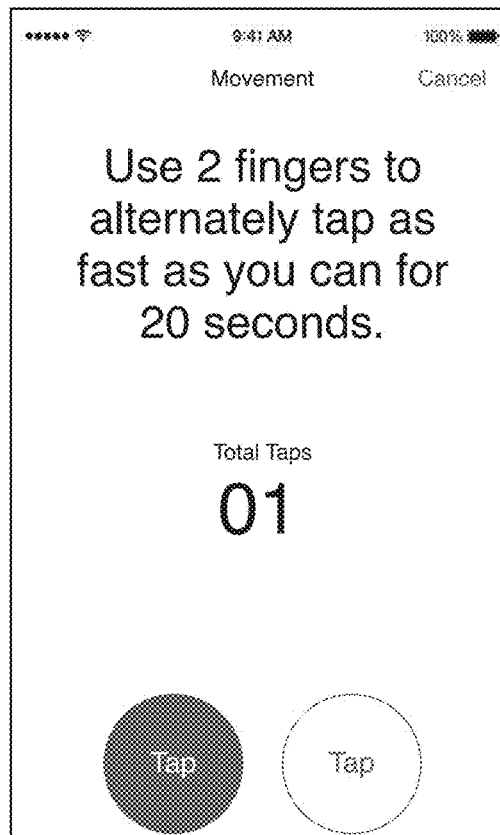
Figure 9F:
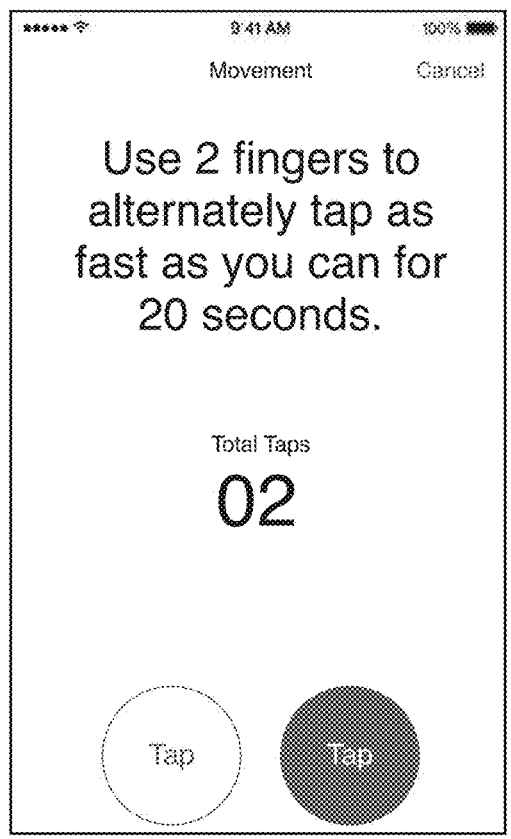
Figure 9G:
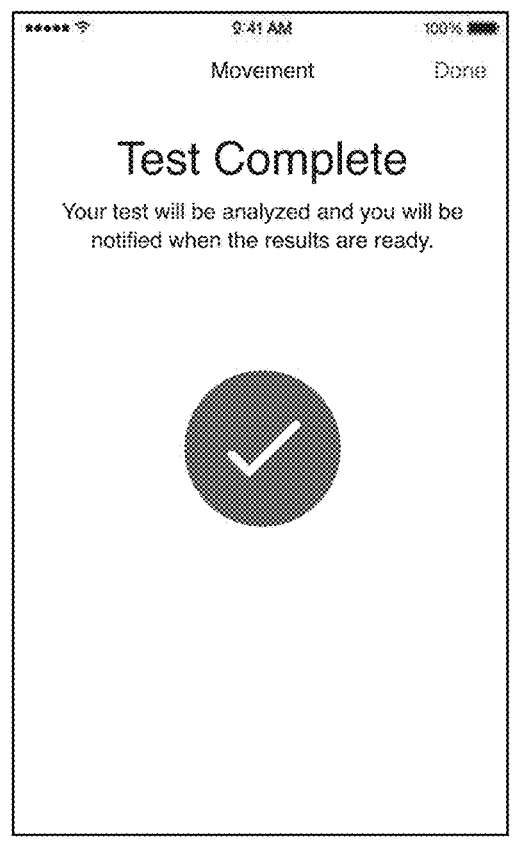
Figure 10A:
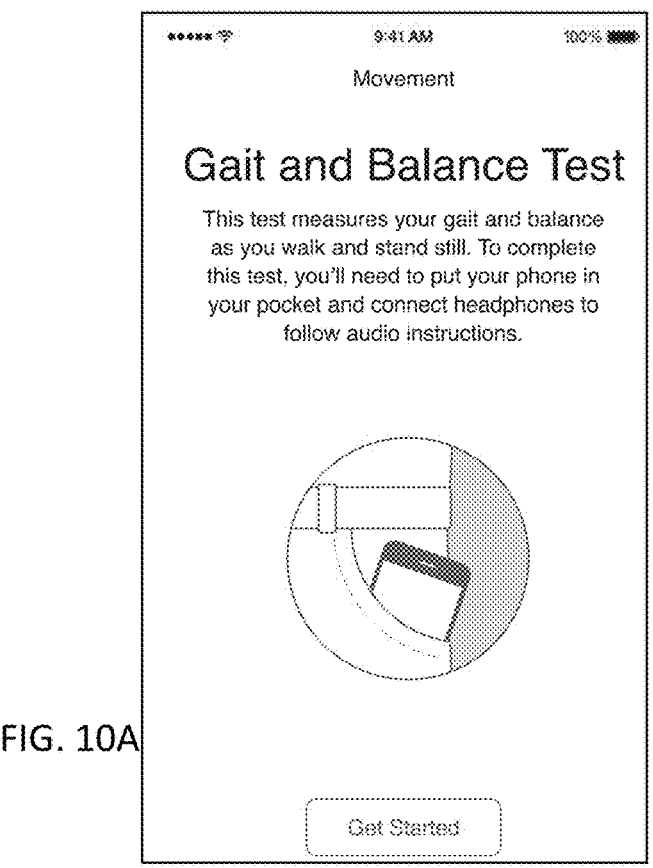
FIG. 10A-10E are example screens pertaining to an activity task module accommodated within the application framework, in accordance with certain embodiments.
Figure 10B:
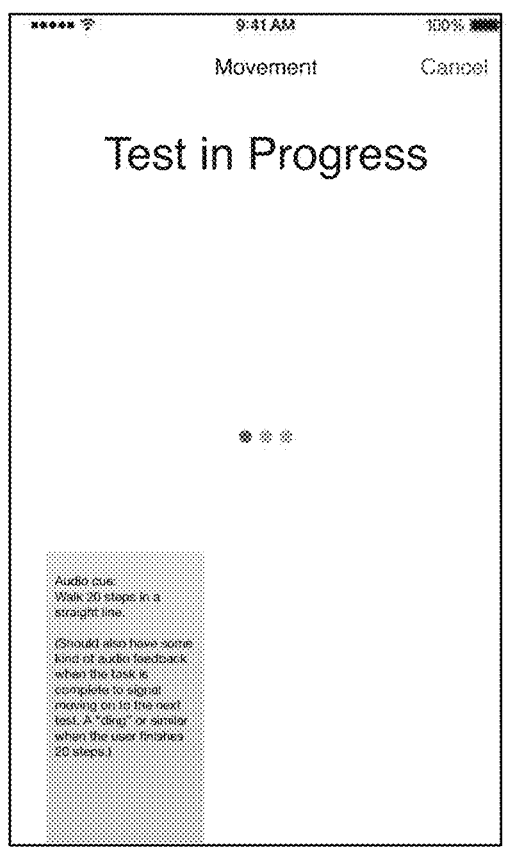
Figure 10C:
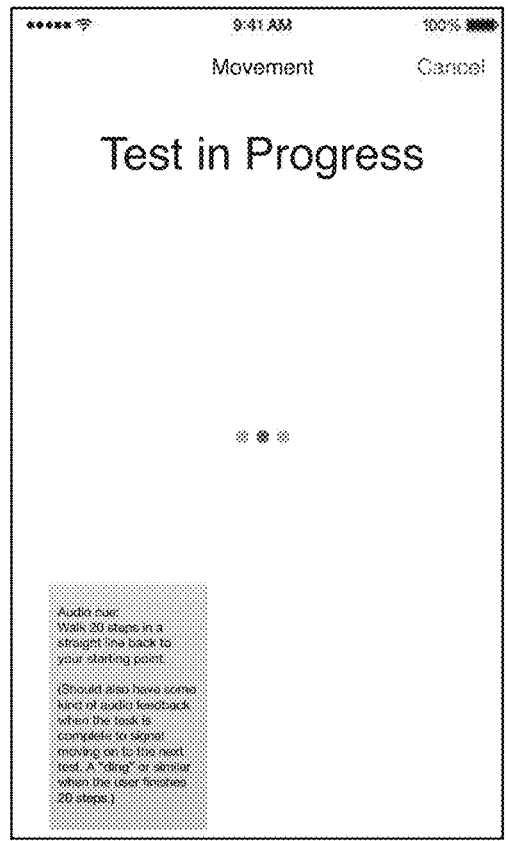
Figure 10D:
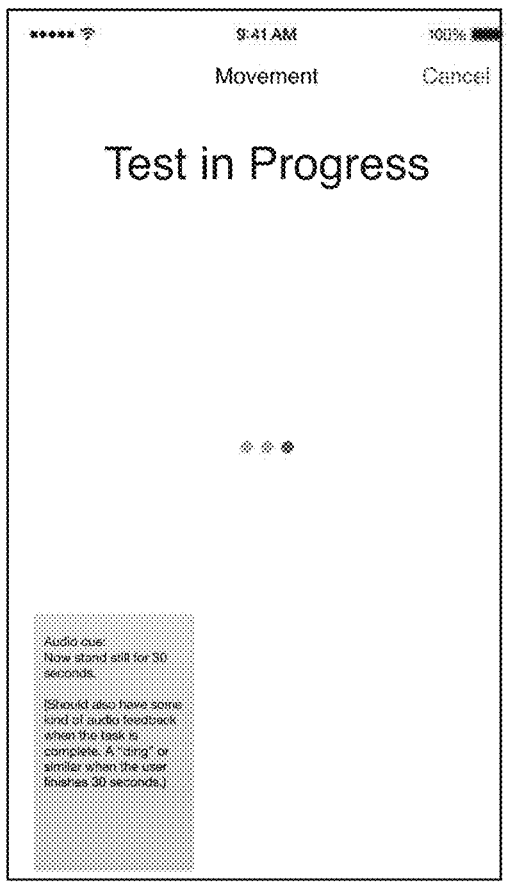
Figure 10E:
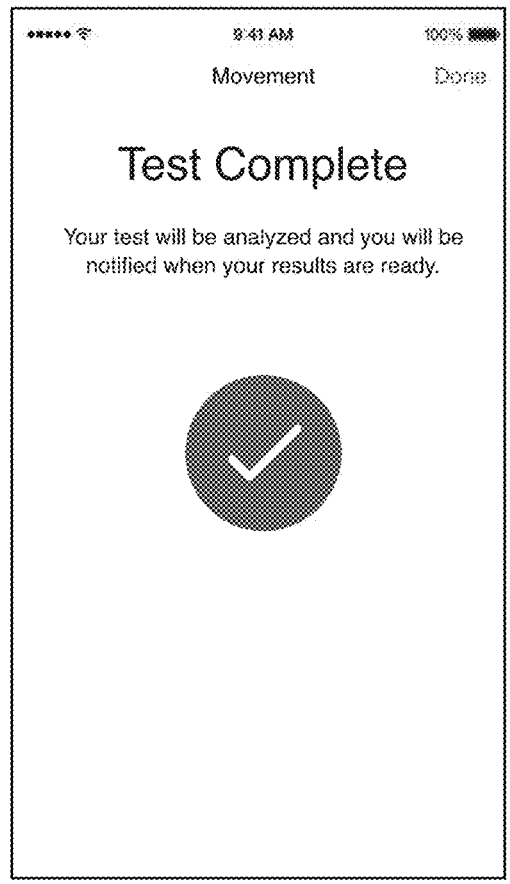
Figure 11A:
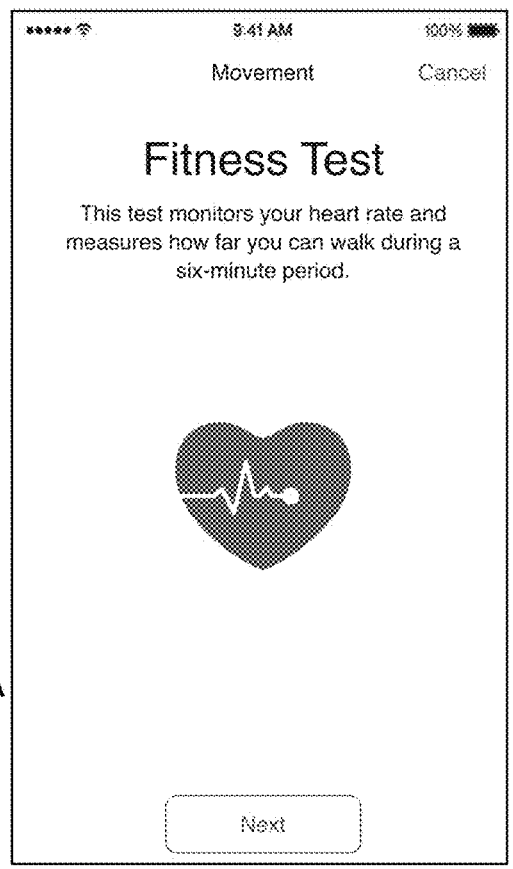
FIG. 11A-11F are example screens pertaining to an activity task module accommodated within the application framework, in accordance with certain embodiments.
Figure 11B:
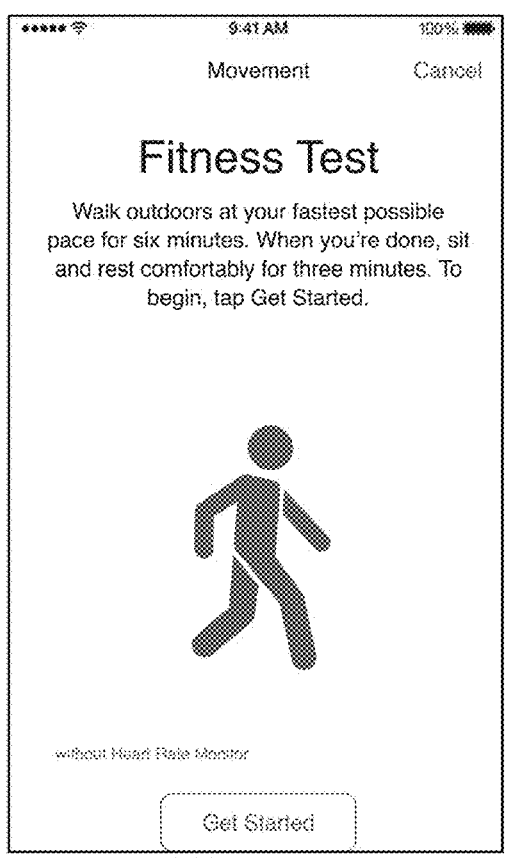
Figure 11C:
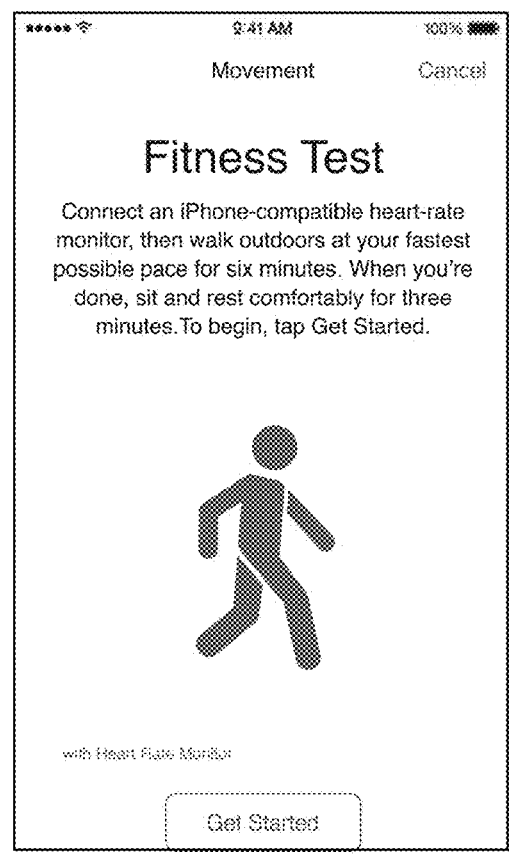
Figure 11D:
Figure 11E:
Figure 11F:
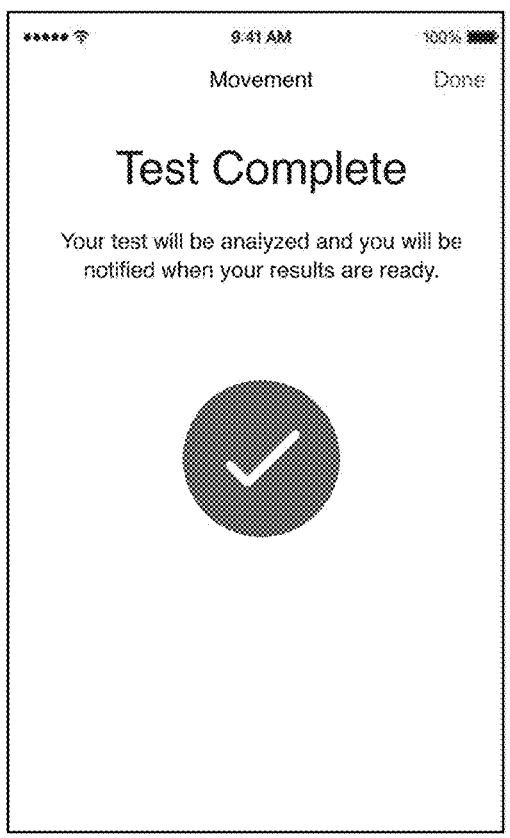

The resulting presentation for these steps looks may produce display screens on the user device similar to those in FIGS. 5A-5B. Additional examples of screens corresponding to Survey Modules are illustrates in FIG. 7A-7C.

In one aspect, the survey module is implemented by use of the task view controller of the portable computing device and the specific it instantiates in order to present the steps. For example:

- the task view controller implements UI state restoration so that it is easy for an application developer to apply state restoration to its hierarchy.
- the task view controller keeps track of what permissions will be needed in order to complete the task, and requests them appropriately after the instructions, but before the results gathering begins. This is done by making calls out to a health information database accessible by the portable device (typically including passively collected health information from one or more wearable device), and other public application program interfaces to request permission to access the required resources. If the user denies access, the task may still continue if it possible to obtain some value from doing so; otherwise an error may be returned to the developer to indicate the task should be cancelled. the task view controller keeps track of the results of question and form steps, so that if the user navigates back through a question, their answers are still available as defaults when they navigate forward again.

1. Instruction Step

Figure 5C:
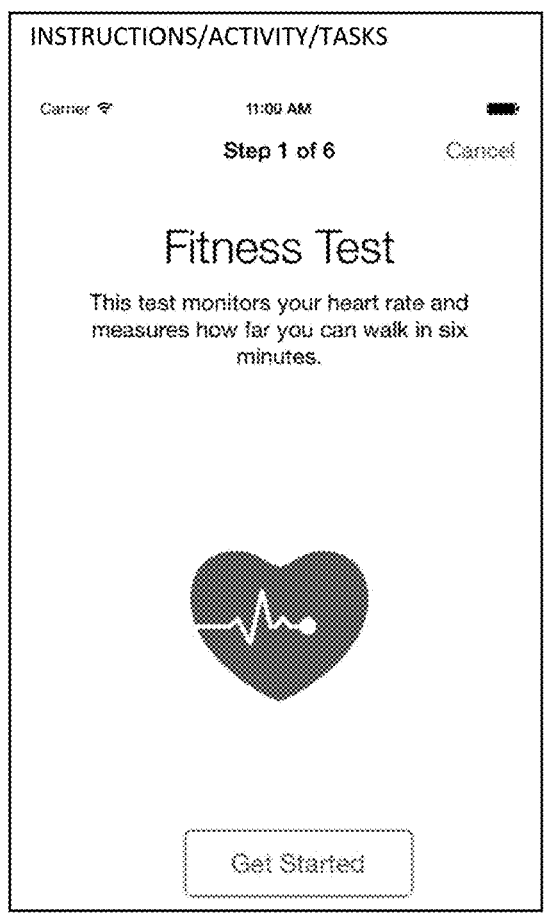

An instruction step can be used to give instructions, or to introduce a task or a new section of a task, when there is no need to obtain a specific result. An instruction step can have an identifier, title, text, detailText, and may have an image. An instruction step produces a simple RKResult with no children, to indicate that the user saw the instruction. An example of such an instruction step is shown in FIG. 5C, which indicates to a user that the Fitness Test Module will be performed.

2. Question Step

Figure 5D:
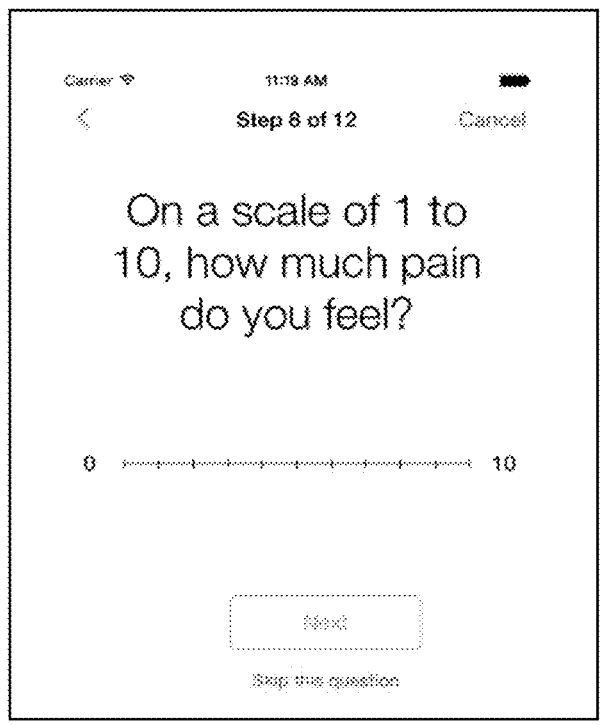
Figure 5E:
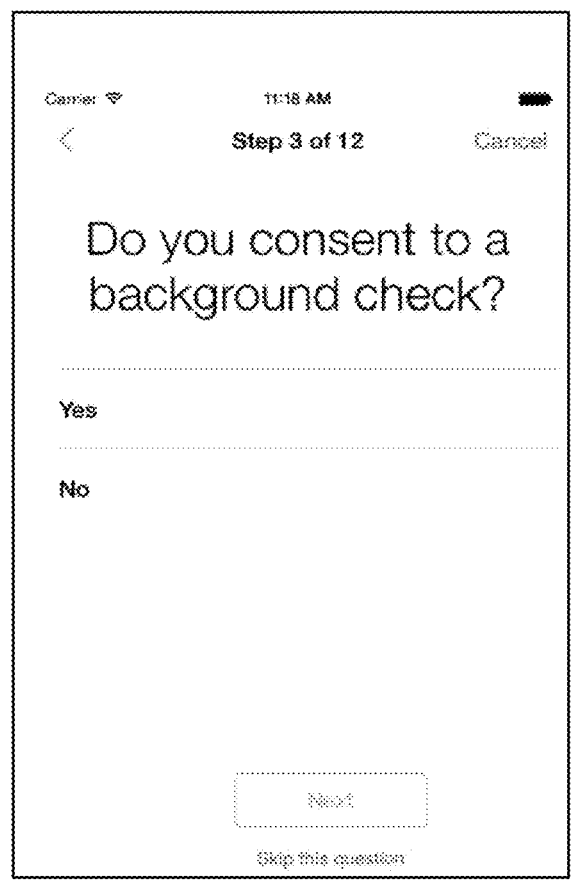
Figures 5F, 5G, 5H:
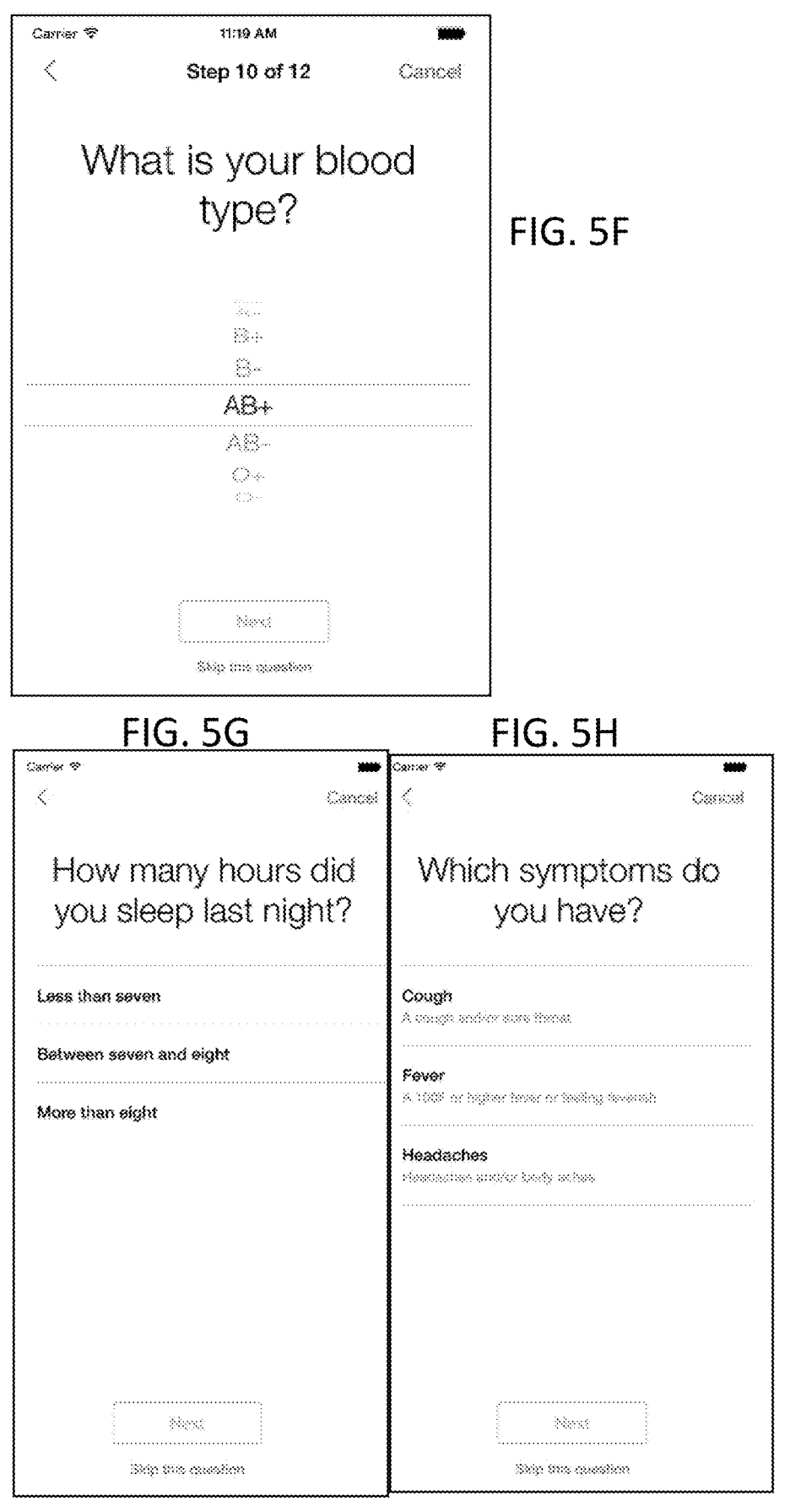
Figures 5I, 5J, 5K:
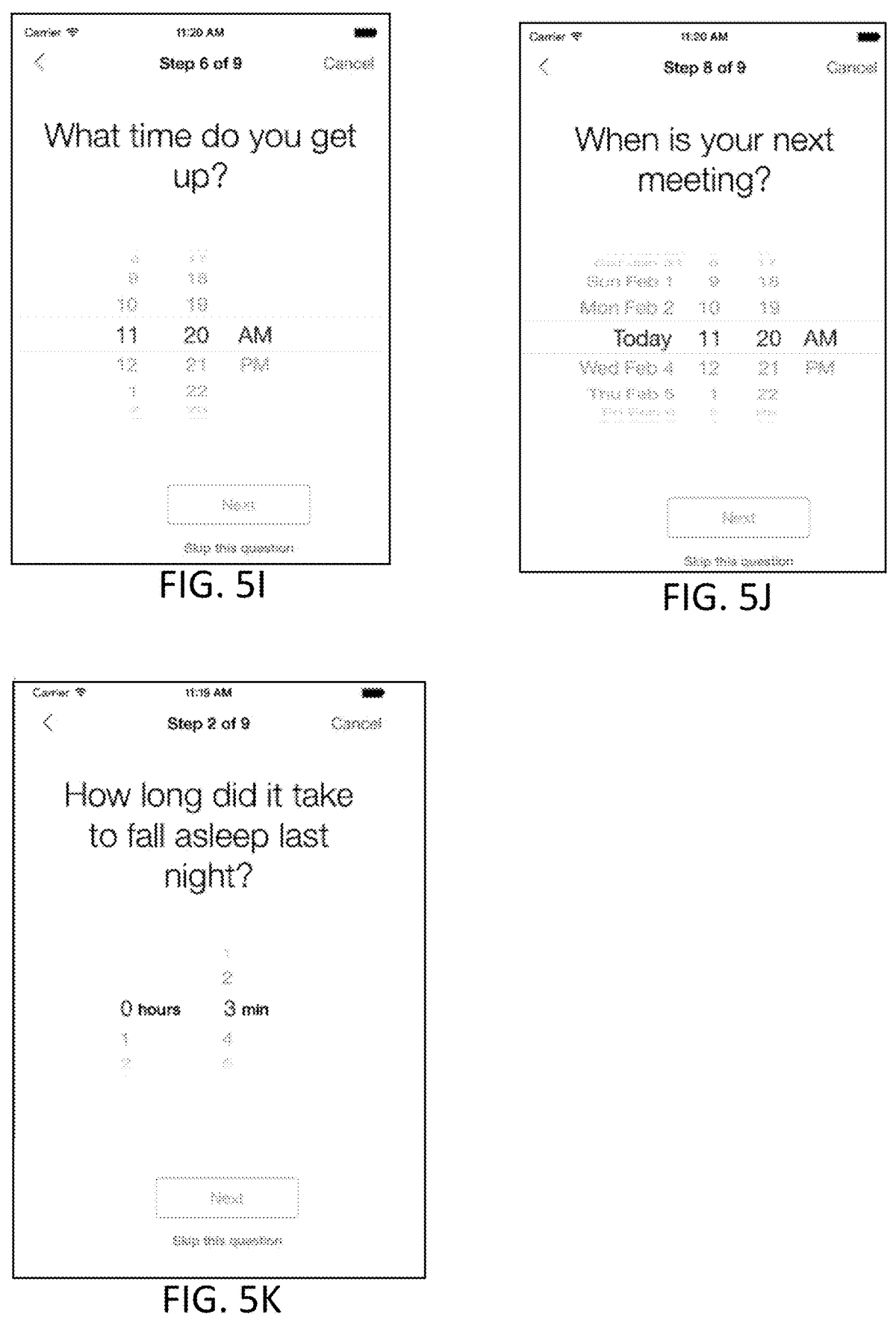
Figure 6A:
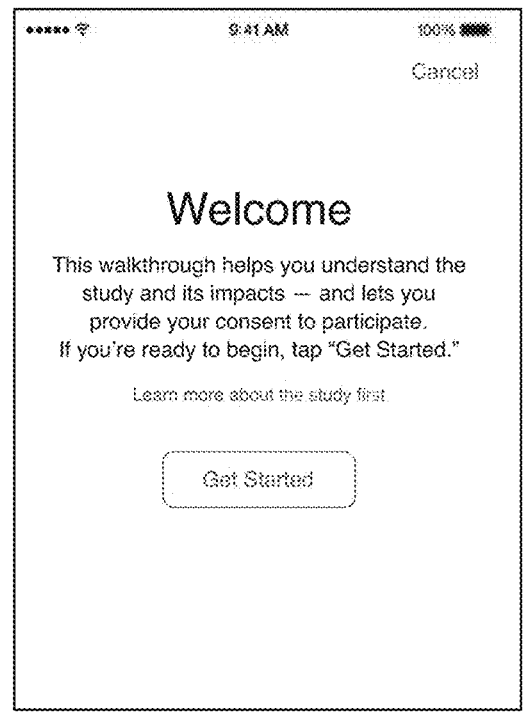
FIG. 6A-6O are example screens displayed on the portable device of the research participant that pertain to a specialized consent module accommodated by the application framework, in accordance with certain embodiments.
Figure 6B:
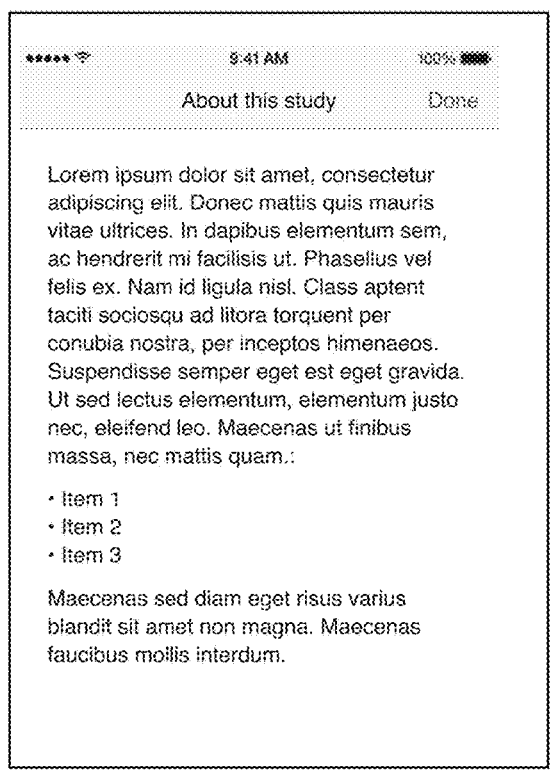
Figure 6C:
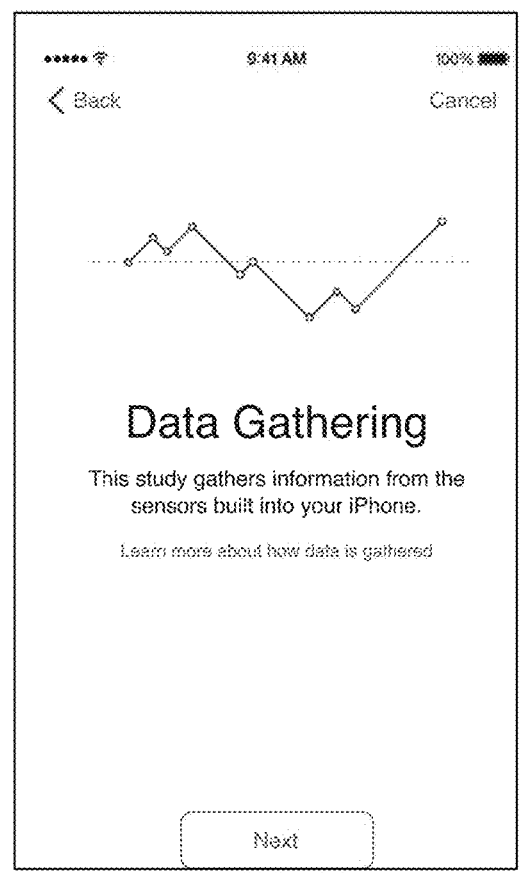
Figure 6D:
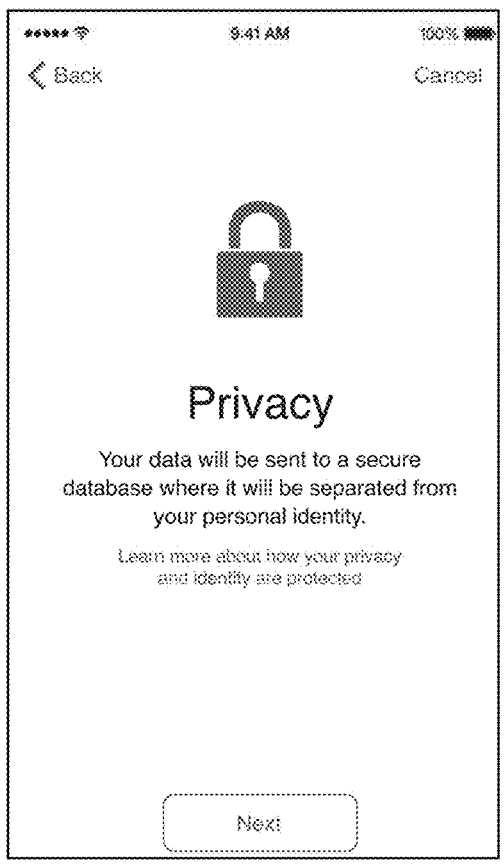
Figure 6E:
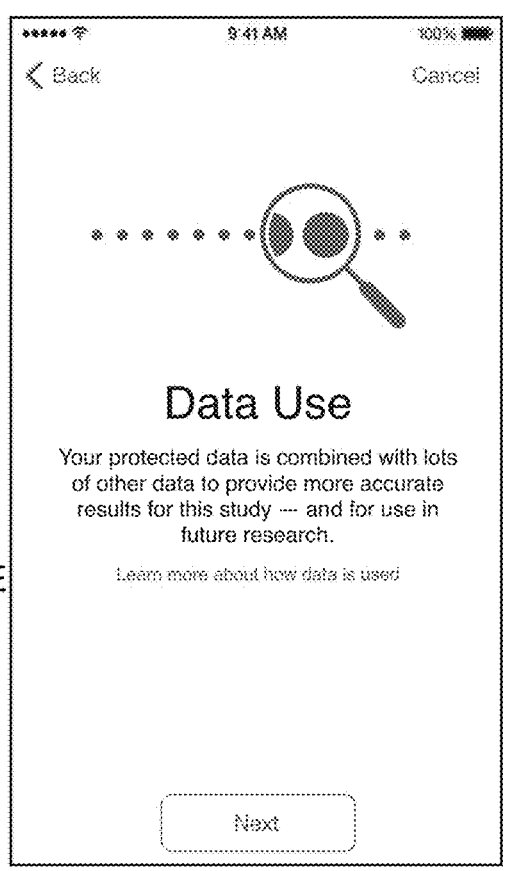
Figure 6F:
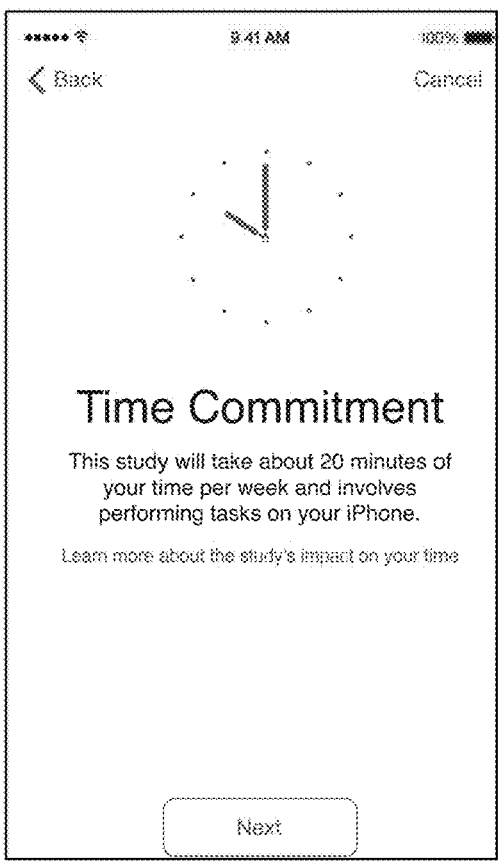
Figure 6G:
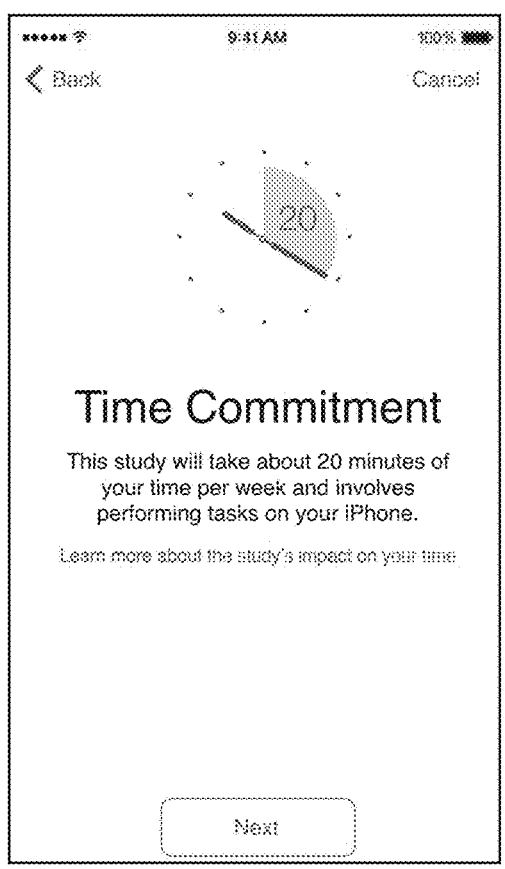
Figure 6H:
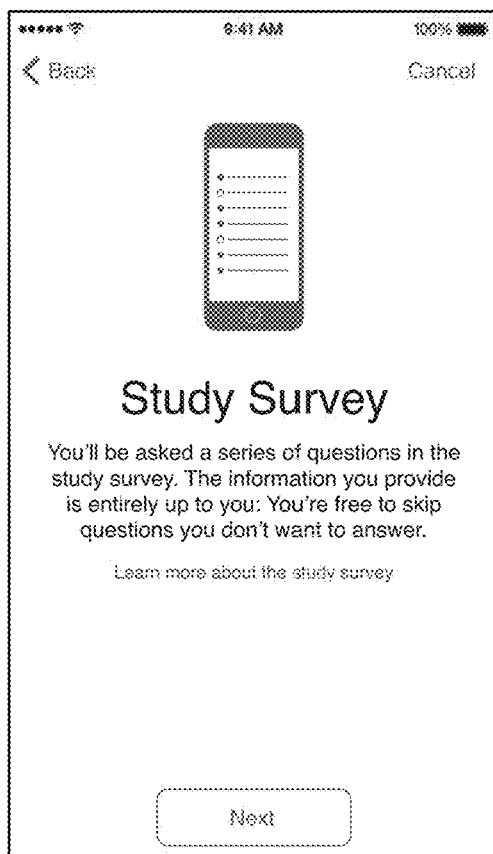
Figure 6I:
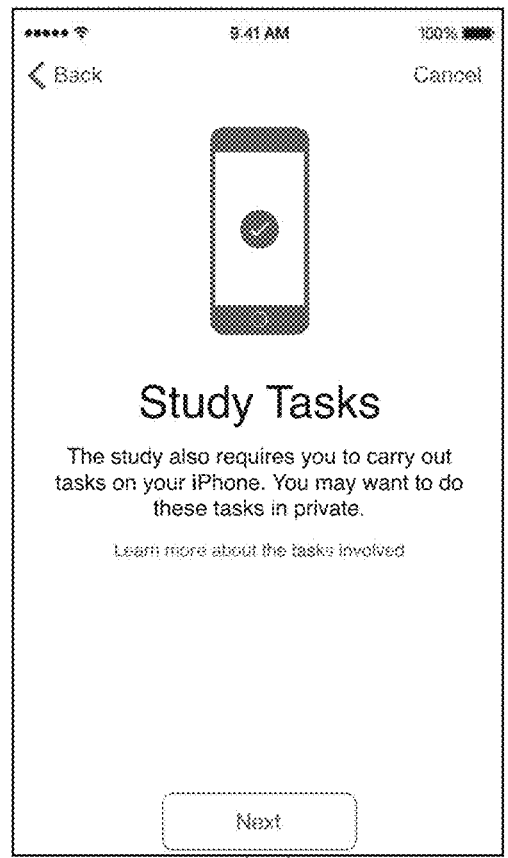
Figure 6J:
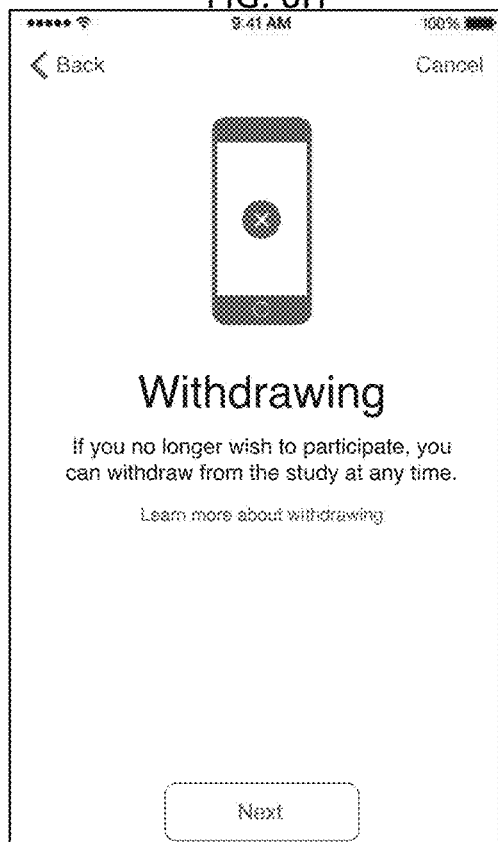
Figure 6K:
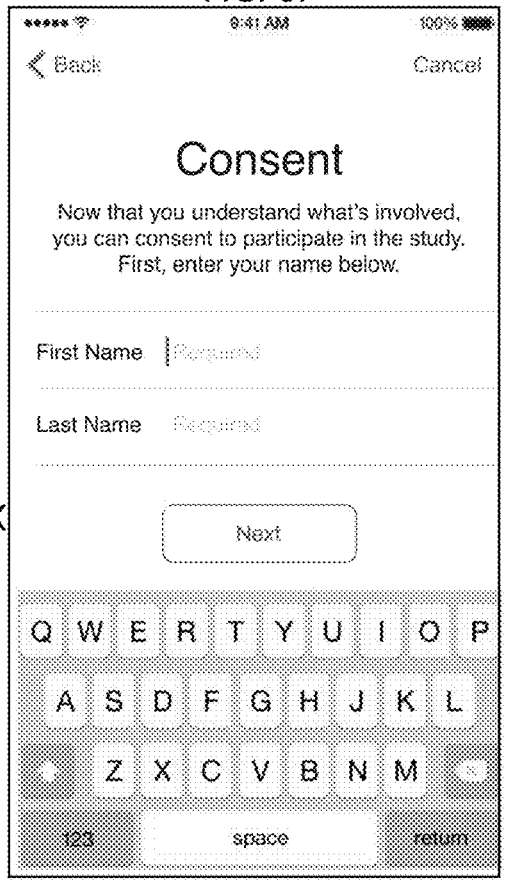
Figure 6L:
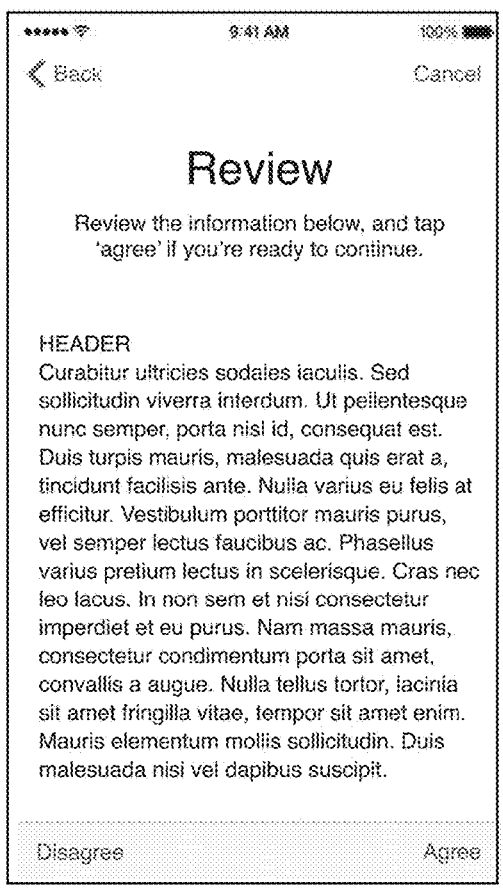
Figure 6M:
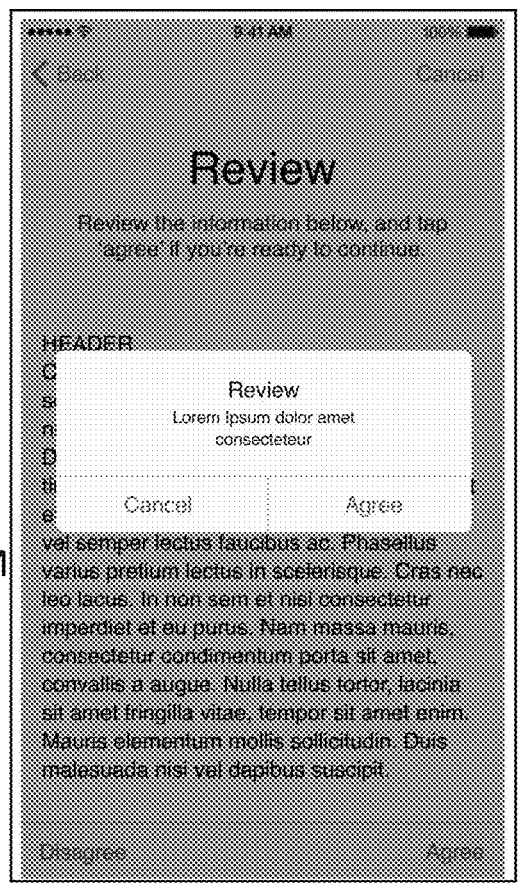
Figure 6N:
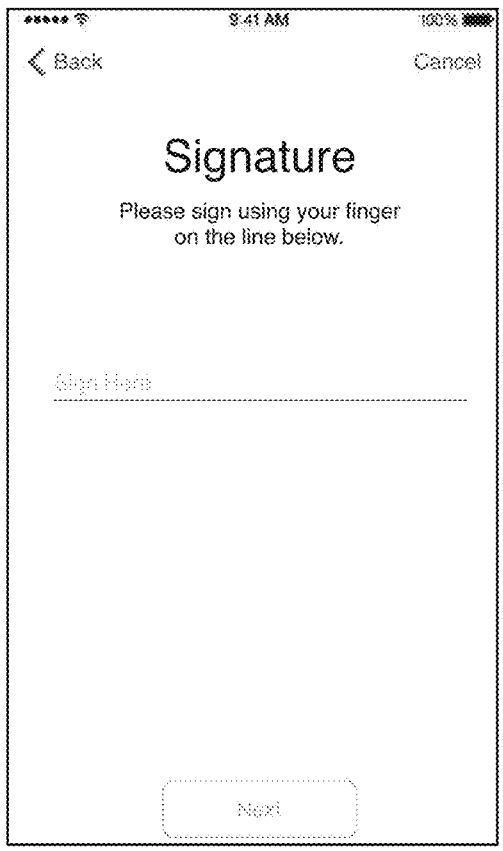
Figure 6O:
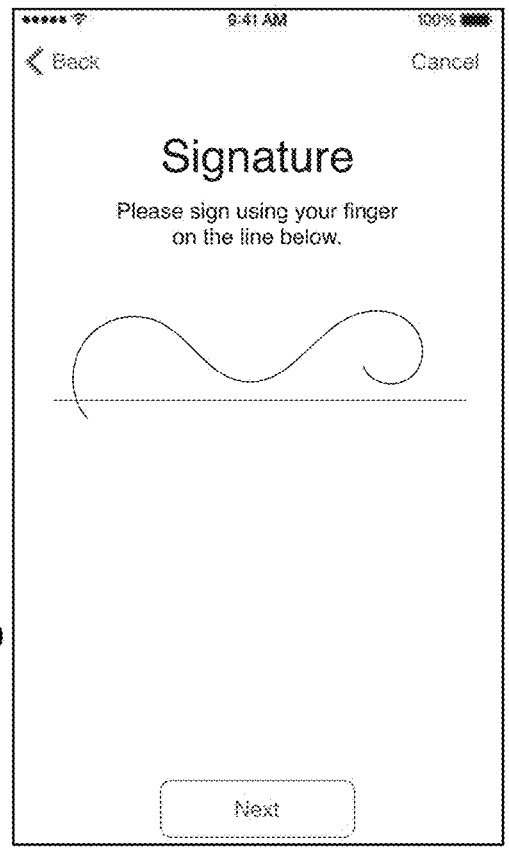

A question step can be used to present a single question at a time or multiple questions according to particular sequence. A question step has an identifier, text, title, answer format, and a placeholder. In addition, question steps can be marked optional if the user can choose not to answer a question. The answer format describes the parameters of the question and how it should be asked. Many of the answer formats support default values. Supported answer formats include: a scale answer format, which presents a slider which the user can use to select values on a scale (see FIG. 5D); a Boolean answer format. (e.g. "Yes" or "No") (see FIG. 5E); a Value picker answer format. Presents a set of text choices using a UIPickerView (e.g. spinning wheel)(see FIG. 5F); an image choice answer format, which presents an image scale, where the developer supplies the images on the scale and appropriate labels for each; a text choice answer format that presents a list of options in a table format for use in either multiple or single choice, which is particularly useful where details are needed to qualify the choices (see FIGS. 5G-5H); numeric answer format in either decimal or integer answers, the range of which can optionally be limited by application of a unit, minimum, or maximum; time of day answer format, which can use a UIDatePicker to let the user select a time of day (see FIG. 5I) or a time and date (FIG. 5J); a time interval answer format that uses a UIDatePicker to let the user select a time interval (see FIG. 5K); and a text answer format, such as a free-form text entry, which may be limited to a certain length of number of characters (see FIGS. 5L-5M), the length of which can be limited In one aspect, where certain questions are asking for data that the user may have already entered into another Health Data Tracking Application on the user device, facility is provided to use an answer format of a characteristic or quantity type. When an answer format common to the Health Data Tracking Application is used, the presentation details can be populated automatically, and the default value may be looked up from the health information database associated with the Health Data Tracking Application, once the user has granted permission for the Application Framework to read those value.

3. Form Step

In one aspect, a form step is similar to a question step in a Survey Module, but a form step supports having multiple questions on a single page. Each question is represented by an RKFormItem, which has an answer format (just like a question step). A form supports all the same answer formats as question steps is shown in the example of FIG. 5N.

B. Informed Consent

When researchers conduct studies involving human subjects, they are typically required to acquire approval for their study design from an ethics committee or, in the US, institutional review board (IRB). For some studies, the IRB will require informed consent, that is, that the researcher must ensure that each participant is fully informed about the nature of the study, and obtain signed consent to participate. Some studies which are deemed of low risk may have this requirement waived, but even in that case it may be useful to offer the information anyway.

The Application Framework includes code to provide a user interface flow for informed consent, to present the researcher's informed consent document, and to obtain their name and optionally a scribbled signature to indicate their consent. Application Framework can also optionally generate a PDF record of the consent, where that is useful for the researchers' workflow.

Use of any part of this informed consent support is optional; no actual content is included (it must come from the researcher's own informed consent document); and no digital signature facilities are included. That is, if the signature needs to be verifiable and irrevocable, then the developer is responsible for producing a digital signature on the result or generated PDF which can attest to the identity of the participant and the time at which they signed. Usually the researcher/developer would need to have the participant authenticate to a server and generate the digital signature on that server.

In one example, the developer must first generate a model of the consent document:

```
RKConsentDocument* consent = [[RKConsentDocument alloc] init];
consent.title = @"Demo Consent";
consent.signaturePageTitle = @"Consent";
consent.signaturePageContent = @"I agree to participate in this research Study.";
RKConsentSignature *participantSig = [RKConsentSignature signatureForPersonWithTitle:@"Participant" dateFormatString:nil identifier:@"participantSig"];
    [consent addSignature:participantSig];
    RKConsentSignature *investigatorSig = [RKConsentSignature signatureForPersonWithTitle:@"Investigator" dateFormatString:nil identifier:@"investigatorSig" firstName:@"Jake" lastName:@"Clemson" signatureImage:[UIImage imageNamed:@"signature.png"] dateString:@"9/2/15" ];
    [consent addSignature:investigatorSig];
    NSMutableArray* components = [NSMutableArray new];
    NSArray* scenes = @[@(RKConsentSectionTypeOverview),
                @(RKConsentSectionTypeDataGathering),
                @(RKConsentSectionTypePrivacy),
                @(RKConsentSectionTypeDataUse),
                @(RKConsentSectionTypeTimeCommitment),
                @(RKConsentSectionTypeStudySurvey),
                @(RKConsentSectionTypeStudyTasks),
                @(RKConsentSectionTypeWithdrawing)];
    for (NSNumber* type in scenes) {
        RKConsentSection* c = [[RKConsentSection alloc] initWithType:type.integerValue];
        c.summary = @"";
        c.htmlContent = @"";
        [components addObject:c];
    }
    consent.sections = [components copy];
```

Then, given that model, one can construct a task containing a visual consent step and a consent review step. That task can then be presented using the same task view controller as would be used for a survey. In fact, survey questions can be mixed in with these steps, either to divert users who are not appropriate subjects for the study with some lead-in questions, or to include additional information with the consent results.

For example, to create a consent task:

```
    RKVisualConsentStep *step = [[RKVisualConsentStep alloc]
initWithIdentifier:@"visual_consent" document:consent];
    RKConsentReviewStep *reviewStep = [[RKConsentReviewStep alloc]
initWithIdentifier:@"consent_review" signature:consent.signatures[0]
inDocument:consent];
        reviewStep.text = @"";
        reviewStep.reasonForConsent = @"";
    RKOrderedTask *task = [[RKOrderedTask alloc]
initWithIdentifier:ConsentTaskIdentifier steps:@[step,reviewStep]];
    // And then present the task.
```

Once the task completes, the developer can make a PDF from the resulting document using something like this:

```
    RKConsentSignatureResult *signatureResult =
(RKConsentSignatureResult *) [[[taskViewController result]
stepResultForStepIdentifier:reviewStep.identifier] firstResult];
        [signatureResult applyToDocument:document];
        [document makePDFWithCompletionHandler:^(NSData
*pdfData, NSError *error) {
            NSLog(@"Created PDF of size %lu (error = %@)",
(unsigned long) [pdfData length], error);
        }];
```

1. Visual Consent Step

User device display screens associated with the visual consent step of example consent modules are shown in FIGS. 6A-6J. The visual consent step takes a consent document (as outlined below) and presents it as a series of screens with animated transitions. The animations are provided as part of the Application Framework, along with the titles of the sections. However, none of the contents are included with the kit; it is the responsibility of the developer to populate the consent document as appropriate for their study. In addition, custom consent document sections can be added by the developer with their own descriptive images and content. Typically, the animations are videos which are supplied as part of the Application Framework package and displayed using public application program interfaces.

2. Consent Review Step

Examples of the written consent review step are shown in FIGS. 6K-6O. The consent review step presents screens for the participant to enter their name, review the document, and to scribble a signature on screen. The review content is obtained from a consent document object, just like for the visual consent step. The developer can provide the consent content as HTML to obtain whatever formatting is required by their IRB; the internal implementation uses UIWebView and/or WKWebView, both public application program interfaces on iOS.

C. Active Task Modules

Active tasks are more interactive tasks than surveys, where the user may be asked to do something that allows the sensors on the portable computing device to collect data that would be interesting for research.

Many kinds of studies can benefit from this type of task; whether to actually measure the condition of interest, or to discover what other variations in the environment may affect that condition. The Application Framework includes several pre-defined tasks, but the code used to implement these is intended to be easily extensible. This allows the research community to contribute back additional tasks to the Research Application Framework to be made more widely available for research. Typically, the Application Framework does not do any analysis of the data collected by a task. There are as many ways to analyze the data as there are research projects. Instead, the resulting sensor data is generally recorded to RKResult objects in memory which the developer can serialize as needed. Where the data would be too large for in-memory delivery, it is written to disk in the outputDirectory specified by the developer, and referenced by an RKFileResult returned with the rest of the task's results.

Examples of Active Task or Activity Modules include a Audio or Phonation Test; Tapping Interval Test; Gait and Balance Test; and Fitness Test. Typically, in activity tests the module includes an instruction for the user to perform a specified activity, after which the user device concurrently monitors sensor data of one or more sensors configured for measuring a parameter relating to the instructed activity.

1. Audio Task Module

In this task, the participant is asked to make some kind of sound with their voice, and the audio data is collected. In one aspect, this module can be used to measure properties of their voice, such as frequency range, or ability to produce certain sounds. The underlying implementation uses public application program interfaces in AVFoundation to collect this data and present volume indication during recording. No data analysis is done; it is up to the developer to define what analysis is appropriate to the task.

```
+ (RKOrderedTask *)audioTaskWithIdentifier:(NSString *)identifier
            intendedUseDescription:(NSString
            *)intendedUseDescription
                speechInstruction:(NSString *)speechInstruction
            shortSpeechInstruction:(NSString
            *)shortSpeechInstruction
                    duration:(NSTimeInterval)duration
                recordingSettings:(NSDictionary
                *)recordingSettings
                    options:(RKPredefinedTaskOption)
                    options;
```

User device display screens associated with an Audio or Phonation Test Activity Module are shown in FIGS. 8A-8F. The user is instructed to speak or produce certain sounds for a duration of time or for as long as they are able during which an audio sensor, such as a microphone, records parameters of the sound (e.g. intensity, pitch, frequency, duration) which may be used. for example, to analyze speech patterns or vocal symptoms.

2. Tapping Test Module

User device display screens associated with an example Tapping Test Module are shown in FIGS. 9A-9G. In the two finger tapping task, the participant is asked to rhythmically, alternatively, tap two targets on the touch screen. For example, data from this task can be used to assess basic motor capabilities including speed, accuracy, and rhythm. Touch data, and optionally accelerometer data from one or more accelerometer sensors, are collected using public application program interfaces. Again, no analysis is performed on the data; it is up to the developer to determine appropriate analysis. This task can be used to obtain measures related to motor speed and timing.

3. Gait and Balance (Short Walk) Test Module

User device display screens associated with this test are shown in FIGS. 10A-10E. In the short walk task, the participant is asked to walk a short distance, which may be indoors. Typical uses of the data may be to assess stride length, smoothness, sway, or other aspects of the participant's walking by using one or more accelerators sensor devices. The presentation of the short walk differs from the fitness check in that distance is replaced by the number of steps taken, and the walk is split into a series of legs. After each leg, the user is asked to turn and reverse direction.

```
+ (RKOrderedTask *)shortWalkTaskWithIdentifier:(NSString *)identifier
            intendedUseDescription:(NSString
*)intendedUseDescription
            numberOfStepsPerLeg:
            (NSInteger)numberOfStepsPerLeg
                restDuration:(NSTimeInterval)restDuration
options:(RKPredefinedTaskOption)options;
```

4. Fitness Test Module

User device display screens associated with an example Fitness Test Activity Module are shown in FIGS. 11A-11F. In the fitness task, the participant is asked to walk for a specified duration (typically several minutes). During this period various sensor data will be collected and returned via the task view controller's delegate. This would include accelerometer, device motion, pedometer, location, and heart rate data where available. At the conclusion of the walk, if heart rate data is available, the participant is asked to sit down and rest for a period. Data collection continues during this period. By default, the task includes an instruction step which explains what to do during the task, but this can be excluded with an appropriate option. All of these data are collected from various other application program interfaces, and serialized. Typically, no analysis is required to be applied to the data.

```
+ (RKOrderedTask *)fitnessCheckTaskWithIdentifier:(NSString
*)identifier
            intendedUseDescription:(NSString
            *)intendedUseDescription
                walkDuration:
                (NSTimeInterval)walkDuration
                restDuration:(NSTimeInterval)restDuration
                    options:(RKPredefinedTaskOption)
                    options;
```

5. Spatial Span Memory Task Module

User device display screens associated with the Spatial Span Memory Task are shown in FIGS. 12A-12I. In the spatial span memory task, the participant is asked to repeat pattern sequences of increasing length in a game-like environment. In one aspect, the "span" (length of the pattern sequence) is automatically varied during the task, increasing after successful completion and decreasing after failures, in the range from minimumSpan to maximumSpan. The speed of sequence playback is controllable, and the shape of the tap target is customizable. The game finishes when either maxTests tests have been completed, or the patient has made maxConsecutiveFailures errors in a row. This task can be used to assess visuospatial memory and executive function.

The results collected are simply scoring figures derived from the game, along with the details of the games presented and the touch inputs the participant made, for example, as follows:

```
+ (RKOrderedTask *)spatialSpanMemoryTaskWithIdentifier:(NSString *)identifier
            intendedUseDescription:(NSString
*)intendedUseDescription
                initialSpan:(NSInteger)initialSpan
                minimumSpan:(NSInteger)minimumSpan
                maximumSpan:(NSInteger)maximumSpan
playSpeed:(NSTimeInterval)playSpeed
                maxTests:(NSInteger)maxTests
maxConsecutiveFailures:(NSInteger)maxConsecutiveFailures
                customTargetImage:(UIImage
*)customTargetImage
                customTargetPluralName:(NSString
*)customTargetPluralName
                requireReversal:(BOOL)requireReversal
options:(RKPredefinedTaskOption)options;
```

6. Generalized Active Task Support

A step in an active task is just another step subclass, usually paired with a step view controller subclass. The Research Application Framework contains an RKActiveStep and RKActiveStepViewController in its private application program interface subset, which are the base classes that can be used in implementing predefined tasks. Among other things, these support attaching recorder configurations to the steps. A recorder configuration is an object which indicates that data should be collected during the duration of the task from a sensor or database on the device; for instance, HealthKit, CoreMotion, CoreLocation, or audio from AVFoundation. Where these application program interfaces return objects, the Research Application Framework can include support for logging them to JSON files. In one aspect, the underlying implementation for logging uses RKDataLogger, which writes log files to disk, and has facilities for rolling them over when they get too large. In one aspect, this file logging support also uses file protection, so that any sensitive data is protected even while it is within the application sandbox. In one aspect, the Research Application Framework's predefined active tasks use NSFileProtectionCompleteUnlessOpen while writing data to disk, and then change the file protection level on any files generated to NSFileProtectionComplete when the task is complete.

D. Passive Data Collection Modules

In another aspect, the module may be configured to collect data from one or more sensors passively without requiring input from the user. The Application Framework may include a passive data collection element that can be used in an app to easily pull historic data using the another application on the portable computing device, such as a Health Data Tracking Application separate from, but interfaceable with the Research Application Framework. In another aspect, these separate applications may interface through a common Operating System of the portable computing device.

In one example, to do so, the developer instantiates an RKStudyStore and attaches one or more studies to it. Each study can have one or more collectors. Typically there would be one collector per data type; for instance, there might be a heart rate collector, a motion activity collector, a step collector, and so on.

```
RKStudy *study = [store addStudyWithIdentifier:MainStudyIdentifier
            delegate:self
            error:&error];
HKQuantityType *quantityType = (HKQuantityType*) [HKObjectType
quantityTypeForIdentifier:HKQuantityTypeIdentifierStepCount];
RKHealthCollector *healthCollector = [study
addHealthCollectorWithSampleType:quantityType
                unit:[HKUnit countUnit]
                startDate:nil
                error:&error];
HKQuantityType *quantityType2 = (HKQuantityType*) [HKObjectType
quantityTypeForIdentifier:HKQuantityTypeIdentifierBloodGlucose];
HKUnit *unit = [HKUnit unitFromString:@"mg/dL"];
RKHealthCollector *glucoseCollector = [study
addHealthCollectorWithSampleType:quantityType2
                unit:unit
                startDate:nil
                error:&error];
[store resume];
```

Once a study has been configured, when the participant joins the study, the developer can call updateParticipating:withJoinDate:error: to indicate that data collection should start. At this point, the study store will request access to the various data sources (possibly popping up dialogs in the UI of the application). Then, it will start appropriate queries for each data type and start logging the resulting data.
[study updateParticipating:YES withJoinDate:[NSDate date] error:&err];

When new data has been successfully collected from another application or accessible database, such as that associated with a separate Health Data Tracking Application, the developer then has to do something with it. Notifications of the data collection are returned to the delegate to facilitate this. The Research Application Framework includes code which can help with converting those pieces of data to JSON, logging them to disk, and notifying the delegate when the total size of the logs has reached a certain threshold. The final step is to archive the data to a compressed file ready for upload to a server.

When the RKStudyStore and RKStudy are active, each RKHealthCollector will instantiate a observation query for the health information database associated with another application. If the application developer has given their app the appropriate entitlement for that other application (e.g. Health Data Tracking Application), the application will be launched in the background when data of that type has been added. Each time there is new data, the study store will run an HKAnchoredObjectQuery to query for new samples. Internally, the RKStudyStore tracks the last anchor successfully read, so that only new samples are retrieved. The observer query may cause the application to be woken into the background when new data is available. The developer should instantiate the RKStudyStore and resume it, at which point new data will automatically be fetched.

Figure 13:
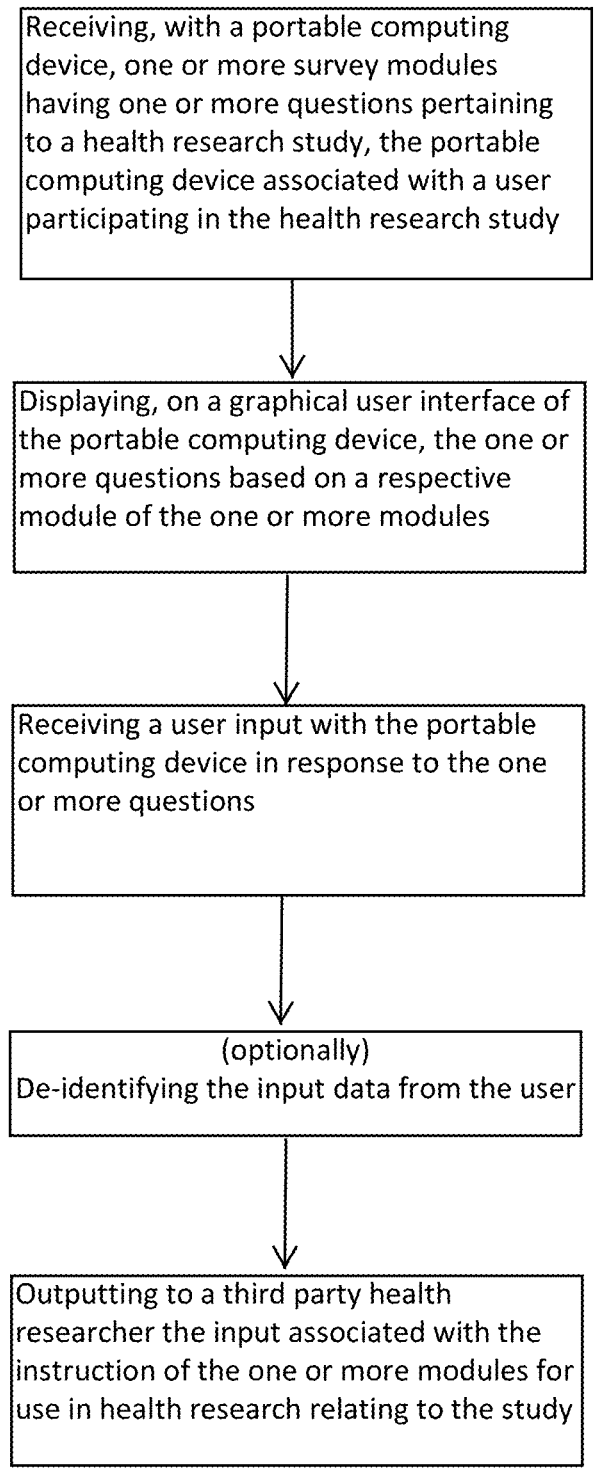
FIGS. 13-14 are flowcharts of methods of facilitating treatment using modules within an application framework of a portable computing device of a user, in accordance with certain embodiments.
Figure 14:
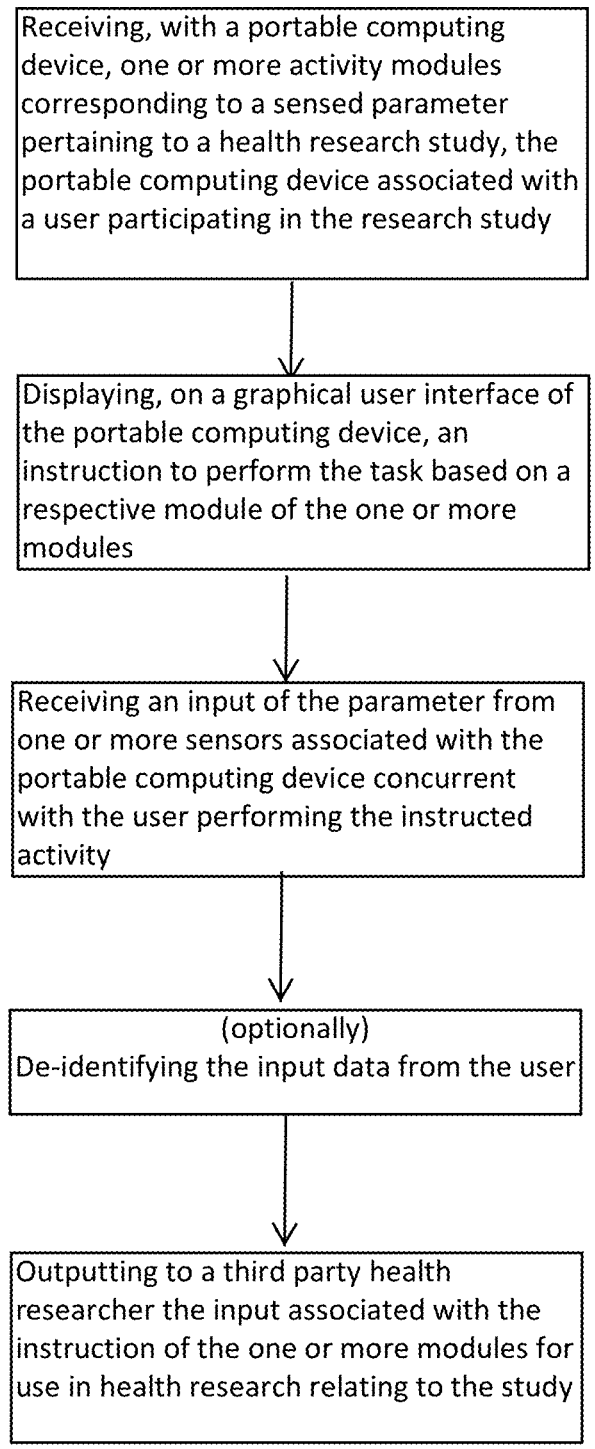

FIGS. 13-14 illustrate example methods of facilitating research with a portable computing device of a user and one or more modules received by the device in accordance with embodiments of the invention. In the example of FIG. 13, the method includes steps of: receiving, with a portable computing device, one or more survey modules having one or more questions pertaining to a health research study, the portable computing device associated with a user participating in the health research study; displaying, on a graphical user interface of the portable computing device, the one or more questions based on a respective module of the one or more modules; receiving a user input with the portable computing device in response to the one or more questions; optionally, de-identifying the input data from the user; and outputting to a third party health researcher the input associated with the instruction of the one or more modules for use in health research relating to the study. In the example of FIG. 14, the method includes steps of: receiving, with a portable computing device, one or more activity modules corresponding to a sensed parameter pertaining to a health research study, the portable computing device associated with a user participating in the research study; displaying, on a graphical user interface of the portable computing device, an instruction to perform the task based on a respective module of the one or more modules; receiving an input of the parameter from one or more sensors associated with the portable computing device concurrent with the user performing the instructed activity; optionally, de-identifying the input data from the user; and outputting to a third party health researcher the input associated with the instruction of the one or more modules for use in health research relating to the study.

Illustrative methods and systems for managing user device connections are described above. Some or all of these systems and methods may, but need not, be implemented at least partially by architectures such as those shown at least in FIGS. 1-14 above. While many of the embodiments are described above with reference to personal and/or health-related information, it should be understood any type of user information or non-user information may be managed using these techniques. Further, in the foregoing description, various non-limiting examples were described. For purposes of explanation, specific configurations and details are set forth in order to provide a thorough understanding of the examples. It is appreciated that the above examples may be practiced without certain specific details and that well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User devices (e.g., client devices) can include any type of general purpose personal computer such as, but not limited to, desktop or laptop computers running a standard operating system, as well as cellular, wireless, and/or handheld devices running mobile software and capable of supporting a number of networking and messaging protocols. These devices can also include other electronic devices, such as dummy terminals, thin-clients, gaming systems, or other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

The environment can include a variety of data stores and other memory and storage media as discussed above. These can reside in a variety of locations, such as on a storage medium local to (and/or resident in) one or more of the computers. Alternatively, the memory can be remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as desired.

The system and various devices may also include one or more software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

What is claimed is:

1. A method for facilitating health research, the method comprising:

storing predefined first-party health research modules in a computer system, wherein each of the predefined first-party health research modules are performable by a health data tracking application that is executable by a portable computing device;

receiving, by the computer system, one or more third-party health research modules and a selection that designates one or more of the predefined first-party health research modules, wherein each of the one or more third-party health research modules are performable by the health data tracking application, wherein the one or more third-party research modules are associated with a health researcher, and wherein the one or more third-party research modules and the one or more of the predefined first party health research modules designated by the selection are associated with a health research study;

transmitting, by the computer system, the one or more third-party health research modules to the portable computing device;

transmitting, by the computer system, the selection and/or one or more of the one or more of the predefined first-party health research modules designated by the selection to the portable computing device;

receiving, by the computer system, subject response data from the portable computing device, wherein the subject response data is generated by the portable computing device in response to input to the portable computing device in response to performance by the portable computing device of the one or more third-party health research modules and the one or more of the predefined first-party health research modules designated by the selection; and transmitting, by the computer system, the subject response data to the health researcher.

2. The method of claim 1 further comprising:

de-identifying the subject response data from the subject before outputting the subject response data to the health researcher.

3. The method of claim 1, wherein the subject response data comprises sensor output generated via one or more sensors associated with the portable computing device.

4. The method of claim 3, wherein the one or more sensors detect any of: activity level, activity tracking, respiration, body temperature, heart wellness data, hydration levels, perspiration, blood glucose, salinity, sleep cycles, posture, O2 levels, muscle engagement, or any combination thereof.

5. The method of claim 3, wherein:
the sensor output is generated over a duration of time; and
the sensor output is generated via measuring a sensor parameter based on an interaction by the subject with the portable computing device.

6. The method of claim 3, wherein the sensor output is passively collected from the one or more sensors without requiring an interaction by the subject with the portable computing device.

7. The method of claim 1, wherein the third-party health research modules and the one or more of the predefined first-party research models designated by the selection effects a survey and/or an activity accomplished by the subject.

8. The method of claim 1, wherein the one or more of the predefined first-party health research modules comprise one or more predefined first-party survey modules that request information from the subject regarding eligibility of the subject to participate in the health research study.

9. The method of claim 1, wherein the one or more of the predefined first- party health research modules comprise one or more predefined first-party consent modules that request input from the subject indicative of consent of the subject to participate in the health research study.

10. The method of claim 3, wherein the one or more of the predefined first-party health research modules comprise one or more predefined first-party active task modules that ask the subject to perform a task during which the sensor output is generated.

11. The method of claim 3, wherein the one or more of the predefined first-party health research modules comprise one or more predefined first-party passive data collection modules configured to collect the sensor output passively without input from the subject.

12. The method of claim 1, further comprising:
receiving health information of the subject from an electronic medical record of the subject;
generating de-identified health information of the subject by de-identifying the health information of the subject from the subject; and
transmitting the de-identified health information of the subject to the health researcher.

13. A computer system for facilitating health research, the computer system comprising:
one or more processors; and
a computer readable medium storing computer executable instructions and predefined first-party health research modules, wherein each of the predefined first-party health research modules are performable by a health data tracking application that is executable by a portable computing device, and wherein the computer executable instructions are executable by the one or more processors to cause the computer system to:
receive one or more third-party health research modules and a selection that designates one or more of the predefined first-party health research modules, wherein each of the one or more third-party health research modules are performable by the health data tracking application, wherein the one or more third-party research modules are associated with a health researcher, and wherein the one or more third-party research modules_and the one or more of the predefined first party health research modules designated by the selection are associated with a health research study;
transmit the one or more third-party health research modules to the portable computing device;
transmit the selection and/or one or more of the one or more of the predefined first-party health research modules designated by the selection to the portable computing device;
receive subject response data from the portable computing device, wherein the subject response data is generated by the portable computing device in response to input to the portable computing device in response to performance by the portable computing device of the one or more third-party health research modules and the one or more of the predefined first-party health research modules designated by the selection; and
transmit the subject response data to the health researcher.

14. The computer system of claim 13, wherein the computer executable instructions are further executable by the one or more processors to cause the computer system to de-identify the subject response data from the subject before outputting the subject response data to the health researcher.

15. The computer system of claim 13, wherein the subject response data comprises sensor output generated via one or more sensors associated with the portable computing device.

16. The computer system of claim 15, wherein the one or more sensors detect any of: activity level, activity tracking, respiration, body temperature, heart wellness data, hydration levels, perspiration, blood glucose, salinity, sleep cycles, posture, O2 levels, muscle engagement, or any combination thereof.

17. The computer system of claim 15, wherein:
the sensor output is generated over a duration of time; and
the sensor output is generated via measuring a sensor parameter based on an interaction by the subject with the portable computing device.

18. The computer system of claim 15, wherein the sensor output is passively collected from the one or more sensors without requiring an interaction by the subject with the portable computing device.

19. The computer system of claim 15, wherein the one or more of the predefined first-party health research modules comprise one or more predefined first-party active task modules that ask the subject to perform a task during which the sensor output is generated.

20. The computer system of claim 15, wherein the one or more of the predefined first-party health research modules comprise one or more predefined first-party passive data collection modules configured to collect the sensor output passively without input from the subject.

21. The computer system of claim 13, wherein the third-party health research modules and the one or more of the predefined first-party research models designated by the selection effects a survey and/or an activity accomplished by the subject.

22. The computer system of claim 13, wherein the one or more of the predefined first-party health research modules comprise one or more predefined first-party survey modules that request information from the subject regarding eligibility of the subject to participate in the health research study.

23. The computer system of claim 13, wherein the one or more of the predefined first-party health research modules comprise one or more predefined first-party consent modules that request input from the subject indicative of consent of the subject to participate in the health research study.

24. The computer system of claim 13, wherein the computer executable instructions are further executable by the one or more processors to cause the computer system to:

receive health information of the subject from an electronic medical record of the subject;

generate de-identified health information of the subject by de-identifying the health information of the subject from the subject; and transmit the de-identified health information of the subject to the health researcher.

25. A computer readable medium storing computer executable instructions executable by one or more processors of a computer system to cause the computer system to:

store predefined first-party health research modules, wherein each of the predefined first-party health research modules are performable by a health data tracking application that is executable by a portable computing device:

receive one or more third-party health research modules and a selection that designates one or more of the predefined first-party health research modules, wherein each of the one or more third-party health research modules are performable by the health data tracking application, wherein the one or more third-party research modules are associated with a health researcher, and wherein the one or more third-party research modules and the one or more of the predefined first party health research modules designated by the selection are associated with a health research study;

transmit the one or more third-party health research modules to the portable computing device;

transmit the selection and/or one or more of the one or more of the predefined first-party health research modules designated by the selection to the portable computing device;

receive subject response data from the portable computing device, wherein the subject response data is generated by the portable computing device in response to input to the portable computing device in response to performance by the portable computing device of the one or more third-party health research modules and the one or more of the predefined first-party health research modules designated by the selection; and transmit the subject response data to the health researcher.

26. The computer readable medium of claim 25, wherein the computer executable instructions are further executable by the one or more processors to cause the computer system to de-identify the subject response data from the subject before outputting the subject response data to the health researcher.

27. The computer readable medium of claim 25, wherein the subject response data comprises sensor output generated via one or more sensors associated with the portable computing device.

28. The computer readable medium of claim 27, wherein the one or more sensors detect any of: activity level, activity tracking, respiration, body temperature, heart wellness data, hydration levels, perspiration, blood glucose, salinity, sleep cycles, posture, O2 levels, muscle engagement, or any combination thereof.

29. The computer readable medium of claim 27, wherein:

the sensor output is generated over a duration of time; and the sensor output is generated via measuring a sensor parameter based on an interaction by the subject with the portable computing device.

30. The computer readable medium of claim 27, wherein the sensor output is passively collected from the one or more sensors without requiring an interaction by the subject with the portable computing device.

31. The computer readable medium of claim 27, wherein the one or more of the predefined first-party health research modules comprise one or more predefined first-party active task modules that ask the subject to perform a task during which the sensor output is generated.

32. The computer readable medium of claim 27, wherein the one or more of the predefined first-party health research modules comprise one or more predefined first-party passive data collection modules configured to collect the sensor output passively without input from the subject.

33. The computer readable medium of claim 25, wherein the third-party health research modules and the one or more of the predefined first-party research models designated by the selection effects a survey and/or an activity accomplished by the subject.

34. The computer readable medium of claim 25, wherein the one or more of the predefined first-party health research modules comprise one or more predefined first-party survey modules that request information from the subject regarding eligibility of the subject to participate in the health research study.

35. The computer readable medium of claim 25, wherein the one or more of the predefined first-party health research modules comprise one or more predefined first-party consent modules that request input from the subject indicative of consent of the subject to participate in the health research study.

36. The computer readable medium of claim 25, wherein the computer executable instructions are further executable by the one or more processors to cause the computer system to:

receive health information of the subject from an electronic medical record of the subject;

generate de-identified health information of the subject by de-identifying the health information of the subject from the subject; and transmit the de-identified health information of the subject to the health researcher.

* * * * *